(12) United States Patent
DeHarde et al.

(10) Patent No.: US 8,100,844 B2
(45) Date of Patent: *Jan. 24, 2012

(54) AMBULATING ANKLE AND KNEE JOINTS WITH BIDIRECTIONAL DAMPENING AND ASSISTANCE USING ELASTOMERIC RESTRAINT

(75) Inventors: Mark DeHarde, Pottstown, PA (US); Yevgeniy Vinshtok, Allentown, PA (US)

(73) Assignee: Ultraflex Systems, Inc., Pottstown, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/600,362

(22) Filed: Nov. 15, 2006

(65) Prior Publication Data

US 2007/0270976 A1    Nov. 22, 2007

Related U.S. Application Data

(63) Continuation-in-part of application No. 10/423,435, filed on Apr. 25, 2003, now Pat. No. 7,517,330.

(60) Provisional application No. 60/736,922, filed on Nov. 15, 2005.

(51) Int. Cl.
*A61F 5/00* (2006.01)

(52) U.S. Cl. .................. 602/16; 602/20; 602/23; 602/26

(58) Field of Classification Search ................ 602/5, 16, 602/20–27; 128/882
See application file for complete search history.

(56) References Cited

U.S. PATENT DOCUMENTS

| | | |
|---|---|---|
| 1,847,823 A | 3/1932 | Dresser |
| 2,067,567 A | 1/1937 | Gruca |
| 2,832,334 A | 4/1958 | Whitelaw |
| 2,943,622 A | 7/1960 | Nelson |
| 3,707,963 A | 1/1973 | Keropian |
| 3,814,419 A | 6/1974 | Bjorklund et al. |
| 3,826,251 A | 7/1974 | Ross |

(Continued)

FOREIGN PATENT DOCUMENTS

EP    0 522 484 A1    1/1993

(Continued)

OTHER PUBLICATIONS

International Preliminary Examination Report; International Application No. PCT/US03/12887; International Filing Date Apr. 25, 2003; 3 pages.

*Primary Examiner* — Michael A. Brown
(74) *Attorney, Agent, or Firm* — Blank Rome LLP

(57) ABSTRACT

A hinge or joint assembly includes a first member movably connected to a second member to allow angular displacement of the first member relative to the second member in each of extension and flexion (clockwise and counterclockwise) directions, where one elastomeric spring restrains angular displacement in a flexion position, and another elastomeric spring restrains angular displacement in an extension position. In each direction, the angular movement is dampened through compression of the respective elastomeric spring. After dampening the movement in either direction, returning movement is assisted through decompression of the respective elastomeric spring. Alternatively, one or more elastomeric springs are arranged to both dampen through compression and assist through decompression angular movement in each of the flexion and extension directions. The elastomeric spring can provide a pre-determined force deflection curve in compression and an independent rate of return hysteresis in decompression. The elastomeric springs could be urethane.

23 Claims, 30 Drawing Sheets

U.S. PATENT DOCUMENTS

| | | |
|---|---|---|
| 4,252,111 A | 2/1981 | Fletcher et al. |
| 4,310,154 A | 1/1982 | Kauffman |
| 4,340,041 A | 7/1982 | Frank |
| 4,397,308 A | 8/1983 | Hepburn |
| 4,485,808 A | 12/1984 | Hepburn |
| 4,489,718 A | 12/1984 | Martin |
| 4,493,316 A | 1/1985 | Reed et al. |
| 4,502,472 A | 3/1985 | Pansiera |
| 4,508,111 A | 4/1985 | Hepburn |
| 4,538,600 A | 9/1985 | Hepburn |
| 4,614,181 A | 9/1986 | Karlsson |
| 4,633,867 A | 1/1987 | Kausek et al. |
| 4,657,000 A | 4/1987 | Hepburn |
| 4,697,583 A | 10/1987 | Mason et al. |
| 4,726,361 A | 2/1988 | Farley |
| 4,738,252 A | 4/1988 | Friddle et al. |
| 4,771,768 A | 9/1988 | Crispin |
| 4,817,588 A | 4/1989 | Bledsoe |
| 4,844,057 A | 7/1989 | Hoy |
| 4,846,842 A | 7/1989 | Connolly et al. |
| 4,865,024 A | 9/1989 | Hensley et al. |
| 4,928,676 A | 5/1990 | Pansiera |
| 4,938,206 A | 7/1990 | Harris et al. |
| 4,961,416 A | 10/1990 | Moore et al. |
| 4,982,732 A | 1/1991 | Morris |
| 5,000,169 A | 3/1991 | Swicegood et al. |
| 5,002,044 A | 3/1991 | Carter |
| 5,013,037 A | 5/1991 | Stermer |
| 5,025,801 A | 6/1991 | Callaway |
| 5,031,606 A | 7/1991 | Ring, Sr. |
| 5,036,837 A | 8/1991 | Mitchell et al. |
| 5,092,321 A | 3/1992 | Spademan |
| 5,103,807 A | 4/1992 | Makaran |
| 5,117,814 A | 6/1992 | Luttrell et al. |
| 5,121,747 A * | 6/1992 | Andrews .......................... 607/2 |
| 5,188,584 A | 2/1993 | Petrofsky et al. |
| 5,209,716 A | 5/1993 | Frydman et al. |
| 5,313,942 A | 5/1994 | Platzker |
| 5,358,469 A | 10/1994 | Patchel et al. |
| 5,364,323 A | 11/1994 | Liu |
| 5,382,224 A | 1/1995 | Spangler |
| 5,399,154 A | 3/1995 | Kipnis et al. |
| 5,401,235 A | 3/1995 | Devens |
| 5,409,449 A | 4/1995 | Nebolon |
| 5,421,810 A | 6/1995 | Davis et al. |
| 5,454,769 A | 10/1995 | Chen |
| 5,460,599 A | 10/1995 | Davis et al. |
| 5,476,435 A | 12/1995 | Nimmo |
| 5,538,499 A | 7/1996 | Schwenn et al. |
| 5,658,241 A * | 8/1997 | Deharde et al. .................. 602/5 |
| 5,662,595 A | 9/1997 | Chesher et al. |
| 5,681,267 A | 10/1997 | Molino et al. |
| 5,683,353 A * | 11/1997 | Hamersly ....................... 602/16 |
| 5,749,840 A | 5/1998 | Mitchell et al. |
| 5,776,086 A | 7/1998 | Pansiera |
| 5,830,166 A | 11/1998 | Klopf |
| 5,891,061 A | 4/1999 | Kaiser |
| 5,899,869 A | 5/1999 | Barrack, Jr. et al. |
| 6,010,474 A | 1/2000 | Wycoki |
| 6,060,123 A | 5/2000 | Ogawa |
| 6,080,123 A | 6/2000 | Pansiera |
| 6,471,664 B1 | 10/2002 | Campbell et al. |
| 6,517,503 B1 | 2/2003 | Naft et al. |
| 6,827,343 B2 | 12/2004 | Skiera |
| 7,517,330 B2 * | 4/2009 | Deharde et al. .................. 602/16 |
| 2002/0026136 A1 | 2/2002 | Weihermuller |
| 2007/0270976 A1 | 11/2007 | Deharde et al. |

FOREIGN PATENT DOCUMENTS

| | | |
|---|---|---|
| JP | H06-003309 | 1/1994 |
| JP | H08-511975 | 12/1996 |
| JP | H9-502366 | 3/1997 |
| JP | H10-500602 | 1/1998 |
| JP | 10-138366 | 5/1998 |
| JP | 11-508167 | 7/1999 |
| JP | 2003-33377 | 2/2003 |
| WO | WO 95/01141 | 1/1995 |
| WO | WO 95/01769 | 1/1995 |
| WO | WO 97/00661 | 1/1997 |
| WO | WO 01/12110 A1 | 2/2001 |

* cited by examiner

TORQUE DEPENDENCE ON PLANTARFLEXION/DORSIFLEXION ROM, PRELOAD AND DUROMETER

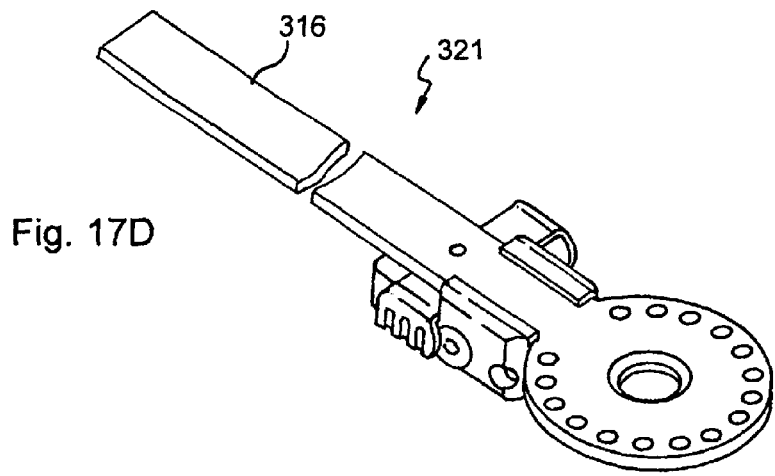
Fig. 17D
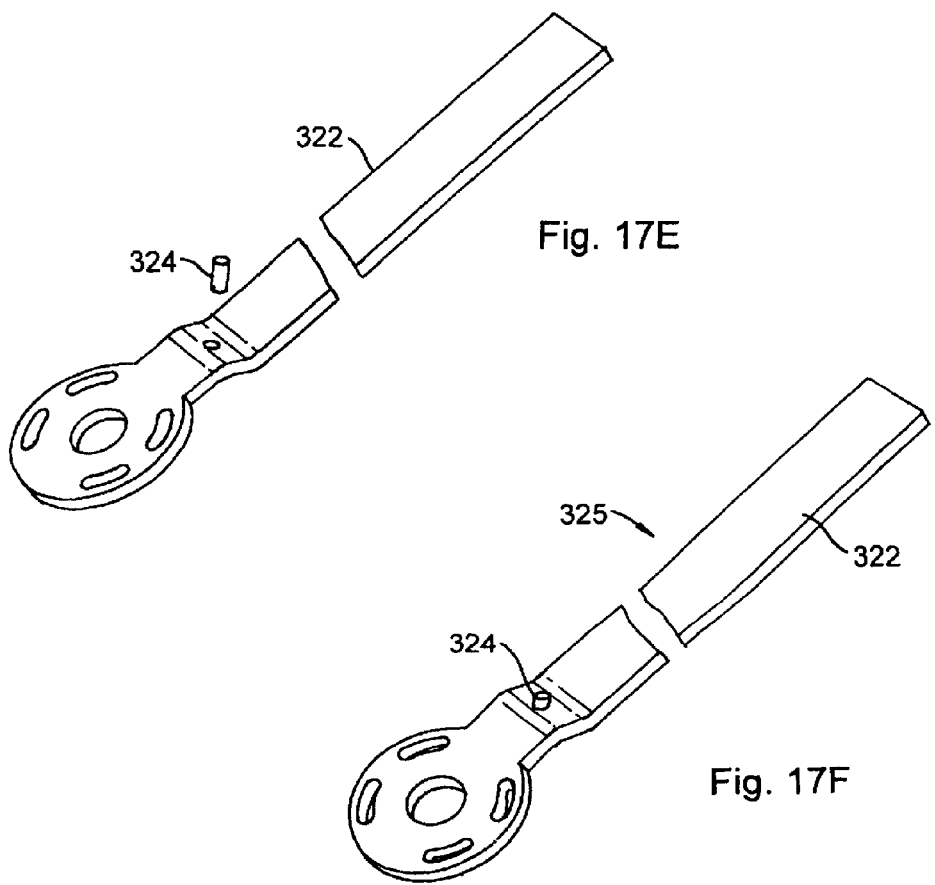
Fig. 17E
Fig. 17F

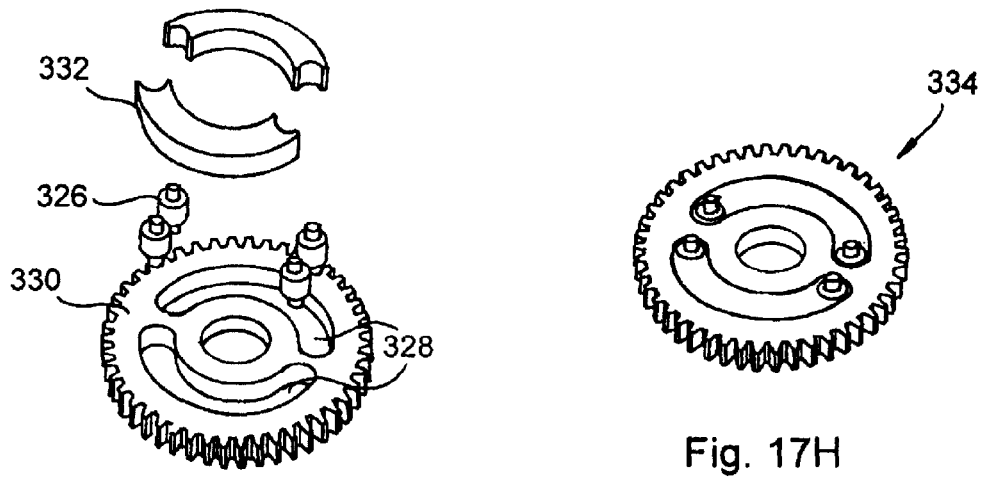
Fig. 17G
Fig. 17H
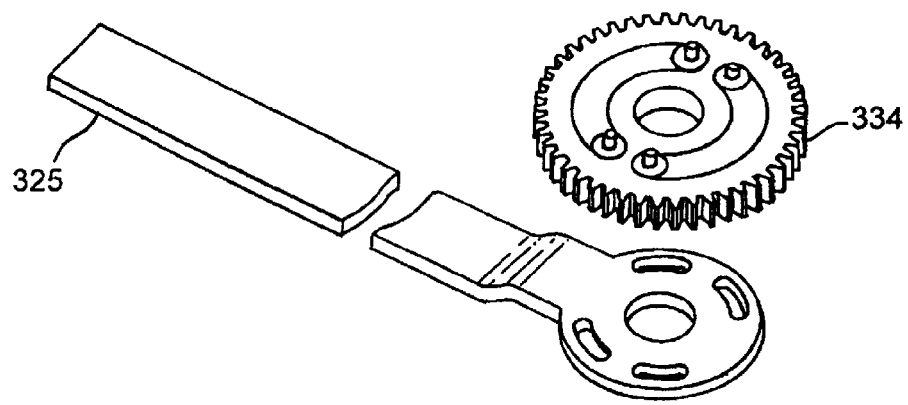
Fig. 17I
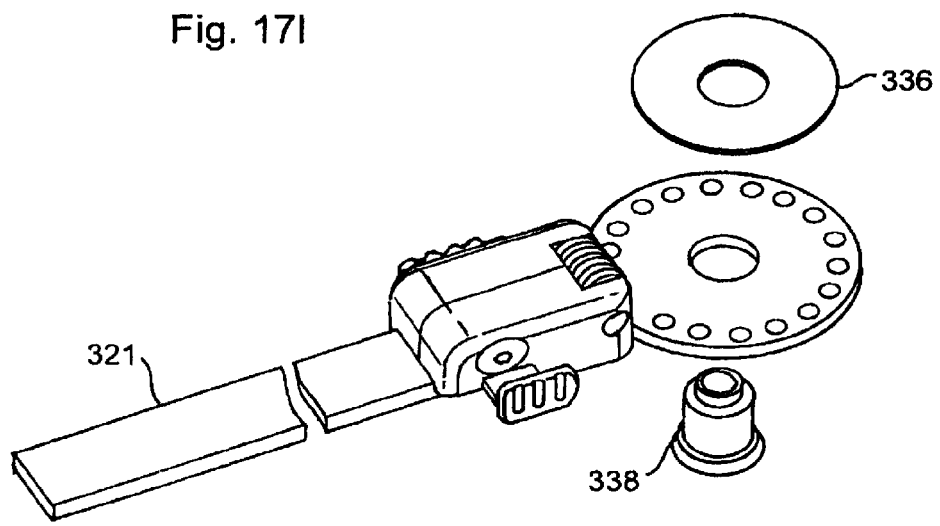

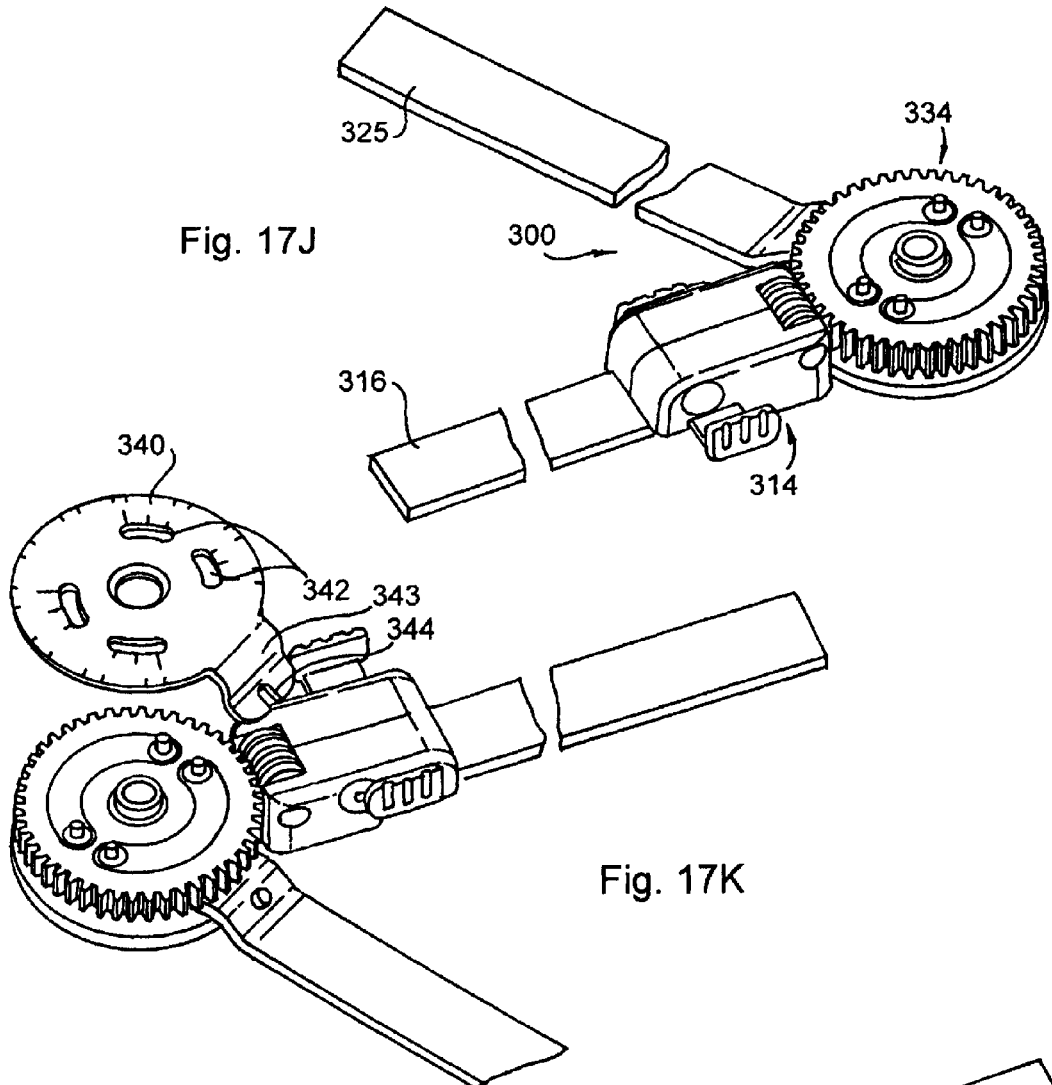
Fig. 17J
Fig. 17K
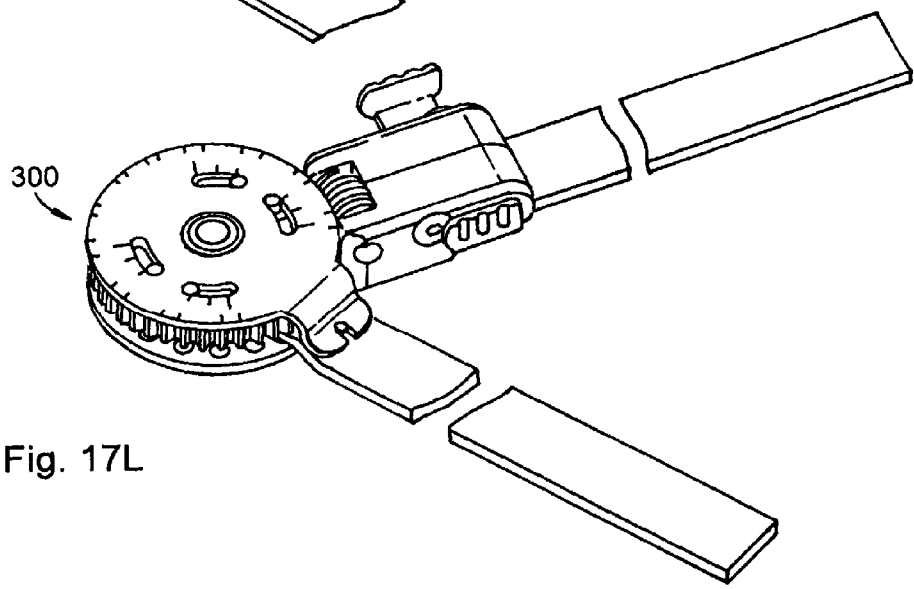
Fig. 17L

AMBULATING ANKLE AND KNEE JOINTS WITH BIDIRECTIONAL DAMPENING AND ASSISTANCE USING ELASTOMERIC RESTRAINT

RELATED APPLICATIONS

This application is a continuation-in-part (CIP) of U.S. application Ser. No. 10/423,435, filed Apr. 25, 2003, entitled "AMBULATING KNEE JOINT," and claims benefit of U.S. Provisional Application Ser. No. 60/736,922, filed Nov. 15, 2005, entitled "AMBULATING ANKLE & KNEE JOINTS WITH BIDIRECTIONAL DAMPENING AND ASSISTANCE USING ELASTOMER RESTRAINTS".

U.S. application Ser. No. 10/423,435 claims benefit of the following U.S. Provisional Applications Application Ser. No. 60/377,119, filed Apr. 25, 2002, entitled "AMBULATING KNEE JOINT WITH RANGE OF MOTION (ROM) DISC AND OVERRIDE FEATURE;" application Ser. No. 60/417,268, filed Oct. 9, 2002, entitled "AMBULATING KNEE JOINT;" application Ser. No. 60/427,777, filed Nov. 20, 2002, entitled "AMBULATING KNEE JOINT;" and application Ser. No. 60/455,809, filed Mar. 19, 2003, entitled "AMBULATING KNEE JOINT." All of the above-noted related applications are incorporated herein by this reference.

FIELD OF THE INVENTION

The present invention relates generally to hinge or joint devices, and more particularly to a hinge or joint assembly for an orthotic, prosthetic, or rehabilitative device capable of supporting the human frame with dynamic shock absorption when walking, while enabling normal, or close to normal, ambulatory motions.

BACKGROUND OF THE INVENTION

A description of a typical human walking cycle (i.e., gait) begins with a heel strike to the ground, followed by a mid-stance phase in which the front of the foot lowers to the ground, pivoting about the grounded heel. The gait then transitions to a toe-off phase, in which the heel is lifted with an associated forward motion of the leg and body on the ball and toes of the foot. Ultimately, the foot is completely lifted from the ground and swung forward in a swing-through phase to the next heel strike. The other foot undertakes the same cycle of motion in a generally coordinated manner to provide forward locomotion.

During this complex motion, each knee transitions from a relatively straight extension at heel strike to a rearward bend, or flexion, through the toe-off phase, and returns to extension during the final swing-through phase. During the cycle, the weight of the patient is borne through the knee to varying degrees. The ankle has similar transitions, first dampening ground reaction forces with toe-off, then re-directing ground reaction force during forward progression, plantarflexion and push-off, and finally dorsiflexion to return the ankle to neutral and assist foot clearance during swing.

The human knee and ankle systems can suffer a number of pathologies that affect the patient's ability to bear this weight and walk (with or without pain). Orthotic ankle and knee devices are primarily directed to supporting and stabilizing the joint in response to muscle weakness and/or joint instability. The devices support, guide, and limit the range of motion of the knee joint during the gait cycle. However, traditional orthotic devices are prone to rigidity in movement, and do not provide flexion and extension capabilities approximating that of a healthy, normal joint. For instance, during a normal walking motion, there exists a certain degree of muscle resistance during ankle or knee flexion, and a certain degree of shock absorption by the quadriceps, for instance, upon heel strike, thereby causing knee flexion and preventing the impact from permeating up the leg to the hips and back, as can occur with a stiff-legged, strutting gait.

For the foregoing reasons, it is an objective of orthotic devices to provide fundamental support, while additionally providing versatility of motion that, to the greatest extent possible, resembles normal joint and muscle function to absorb ground reaction forces and redirect them toward forward progression. Further, an orthotic device closely approximating normal joint and muscle motion can help prevent a learned disuse of certain muscles and movements during a period of prolonged immobility and/or rehabilitation, whereby the brain settles on compensatory muscle use and movements that greatly inhibit mobility, eventually requiring heavier and more restrictive devices resulting in more noticeable limp and an inefficient gait.

SUMMARY OF THE INVENTION

The present invention provides an orthotic, prosthetic, or rehabilitative device that assists, or takes the place of, muscles that are weak or absent, and that normally control and prevent the ankle or knee from lagging during swing-through extension, from buckling at heel strike through terminal stance on the balls and toes of the foot, and from buckling during sit-to-stand from a chair. The device of the present invention provides controlled, multi-position rotational motion in the extension direction to prevent knee buckling from sit-to-stand through a ratcheting, step-advance feature. Further, resistance to ankle and knee flexion is provided through an elastomeric spring, enabling a dampening shock absorption feature, the elastomeric spring also assisting knee movement from a flexed attitude during the swing-phase to a straight leg position (extension) just prior to initial contact with the floor (heel strike). Elastomeric material characteristics further enable relatively high stance control moments to be effectively dampened, while swing return moments and rate of return (or hysteresis) are far less in magnitude and velocity, thereby mimicking normal muscle function.

The present invention provides a weight bearing strut assembly capable of supporting the human frame in the act of walking, while enabling a leg to which it is attached to bend in a normal and natural ambulatory manner. While walking, the present invention provides shock absorption during heel strike and an accelerating or urging capability to a forward moving lower leg during swing from ankle and knee flexion to extension in preparation for receiving weight upon heel strike. Both the dampening, shock absorption function and the urging capability or force is adjustable, with a degree of force and angle of rotation upon which the force is provided being adaptable to suit individual needs. The present invention incorporates the normal and natural ambulatory motion with the security of a step-advance feature, ensuring support of the knee during weight bearing extension (e.g., rising from a sitting position). The elastomeric spring can be adapted to reproduce the force deflection curve of any bodily muscle, by varying the size, shape, and/or characteristics of the elastomeric spring.

The principles and concepts of the present invention can be used in hinge and joint assemblies generally, can be used in an orthotic and/or rehabilitative embodiment as taught and described herein, or can be used in a prosthetic embodiment as modified by those with skill in the art from an appreciation of the present invention. Further, in addition to use in joint and hinge assemblies generally, the present invention can be specifically directed to devices supporting any flexible ligamentous joint, such as the ankle, elbow, or shoulder, and can be adapted to mimicking, assisting, and/or supporting any muscle or tissue, including providing adjustable corrective or therapeutic force for the reduction of joint and muscle stiffness, contracture, or for management of spasticity.

In one aspect of the present invention, a hinge assembly includes a first member movably connected to a second member to allow angular displacement of the first member relative to the second member between extension and flexion positions, and at least one elastomeric spring communicating with the first and the second members to restrain angular displacement from an extension to a flexion position, or from a flexion to an extension position, through compression of the at least one elastomeric spring, and to assist angular displacement from a flexion to an extension position, or from an extension to a flexion position, through decompression of the at least one elastomeric spring. The elastomeric spring can be adapted to provide a pre-determined force deflection curve in compression and an independent rate of return hysteresis in decompression. The elastomeric spring could be a urethane spring.

In another aspect of the present invention, the hinge assembly includes a first member movably connected to a second member to allow angular displacement of the first member relative to the second member between extension and flexion positions, and at least one spring communicating with the first and the second members to dampen angular displacement from an extension to a flexion position, or from a flexion to an extension position, through compression of the at least one spring, and to urge angular displacement from a flexion to an extension position, or from an extension to flexion position, through decompression of the at least one spring, wherein a time rate of compression of the at least one spring in response to a force is faster than a subsequent time rate of decompression of the at least one spring resulting from the force. In this aspect, the at least one spring could be an elastomeric or a torsion spring.

In another aspect of the present invention, the hinge assembly is adapted for an orthotic, prosthetic, or rehabilitative device, and includes a proximal member movably connected to a distal member to allow angular displacement of the proximal member relative to the distal member, a spring housing communicating with the proximal and the distal members, where movement of the spring housing tracks, and is tracked by, movement of one of the proximal or the distal members. In this aspect, the hinge assembly further includes at least one elastomeric spring in bearing engagement with the spring housing, wherein angular displacement of the proximal member relative to the distal member in a first direction compresses the at least one elastomeric spring to dampen the angular displacement in the first direction, where decompression of the at least one elastomeric spring urges angular displacement of the proximal member relative to the distal member in a second direction. The spring housing can include a channel to keep each elastomeric spring, each elastomeric spring then compressing against inner walls of the channel.

In another aspect of the present invention, the hinge assembly is again adapted for an orthotic, prosthetic, or rehabilitative device, and includes a proximal member movably connected to a distal member to allow angular displacement of the proximal member relative to the distal member between extension and flexion positions, and a disk and a lock slide communicating with the proximal and the distal members, the lock slide and the disk adapted for engagement to one another. In this aspect, engagement of the lock slide with the disk over a first pre-determined range arrests angular displacement of the proximal member relative to the distal member in a direction toward flexion, and provides one-way, ratcheting step-advance in a direction toward extension. Further, angularly displacing the disk relative to the proximal and the distal members over a second pre-determined range provides free angular displacement of the proximal member relative to the distal member in a direction toward flexion and toward extension, the free angular displacement occurring over the second pre-determined range even if the lock slide is positioned for engagement of the disk.

In this aspect, the second pre-determined range could be adjustable between approximately 0° to 30° of free angular displacement of the proximal member relative to the distal member in a direction toward flexion and toward extension. The second pre-determined range could occur when the proximal member is positioned between approximately 150° to 180° relative to the distal member. Further, the first pre-determined range could be adjustable between approximately 90° to 120° of angular displacement of the proximal member relative to the distal member in a direction toward flexion and toward extension. The first pre-determined range could occur when the proximal member is positioned between approximately 60° to 180° relative to the distal member.

In this aspect, the hinge assembly could further include a worm gear, and the disk a plurality of worm teeth, the worm gear and the worm teeth being engagably positioned so that operation of the worm gear engages and turns the worm teeth to angularly displace the disk relative to the proximal and the distal members to set the first and the second pre-determined ranges. The lock slide could further includes one or more slide teeth and the disk a plurality of disk teeth, the lock slide engaging the disk by an interlocking of the slide teeth with the disk teeth, the disk teeth and the worm teeth each lying about a perimeter of the disk in a similar plane.

In another aspect of the present invention, a cable release mechanism is provided for an orthotic, prosthetic, or rehabilitative device, and includes an actuator rotatable about an axis and linearly translatable relative to a bearing surface, the actuator having a projecting cam surface and a first and a second operating surface, the cam surface positioned between the first and the second operating surfaces, the cam surface located a greater distance from the axis than the second operating surface, the second operating surface located a greater distance from the axis than the first operating surface, the actuator communicating with a cable and a desired first engagable, and releasably movable, component of the device, the first engagable component releasably moving to engage a second engagable component of the device.

In this aspect, positioning the first operating surface against the bearing surface positions the cable to allow the first engagable component to engage the second engagable component. Positioning the second operating surface against the bearing surface linearly translates the actuator, relative to the bearing surface, to linearly retract the cable, relative to the second engagable component, a distance adequate to disengage the first engagable component from the second engagable component. Finally, positioning the cam surface against the bearing surface linearly translates the actuator, relative to the bearing surface, to linearly retract the cable, relative to the second engagable component, a distance greater than that necessary for positioning either the first or the second operating surface against the bearing surface, thereby causing a toggle action and snap, under cable tension, when moving through cam surface engagement with the bearing surface to either of the first or the second operating surface engagement with the bearing surface, to provide a user with positive and certain positioning of the cable release mechanism. The cable release mechanism could be adapted for employment with any of the hinge assemblies of the present invention.

In another aspect of the present invention, an orthotic, prosthetic, or rehabilitative device is presented and includes a proximal member rotatably connected to a distal member by a hinge assembly, the hinge assembly allowing angular displacement of the proximal member relative to the distal member to and from extension and flexion positions. In this aspect, the hinge assembly includes a disk, a lock slide adapted for engaging the disk, where engagement of the lock slide with the disk, over a first pre-determined range, arrests angular displacement of the proximal member relative to the distal member in a direction toward flexion, and provides one-way, ratcheting step-advance in a direction toward extension. The hinge assembly of this aspect further includes at least one spring communicating with the proximal and the distal members, over a second pre-determined range, to provide a dampening of angular displacement of the proximal member relative to the distal member in a direction toward flexion, and to provide an urging of angular displacement in a direction toward extension. The at least one spring could be a torsion spring or an elastomeric spring.

In this aspect, the hinge assembly could also include a mechanism having a catch, the mechanism angularly communicating with the disk and the proximal and the distal members, where engagement of the lock slide within the catch facilitates the dampening of angular displacement in a direction toward flexion and the urging of angular displacement in a direction toward extension. The mechanism could be a spring housing, the spring housing having a channel to keep each spring, each spring compressing against walls of the channel to dampen the angular displacement in a direction toward flexion and decompressing from walls of the channel to urge the angular displacement in a direction toward extension. Further, at least one post could be fixedly connected to the disk and could extend perpendicularly from a face thereof, each post extending into a respective channel of the spring housing, where each post forcibly bears against a respective spring to compress the spring against the walls of the channel and against the face of the disk to dampen the angular displacement in a direction toward flexion, the spring decompressing against and forcibly moving each post to urge the angular displacement in a direction toward extension. Angular displacement of the spring housing could track, and be tracked by, angular displacement of one of the proximal or the distal members.

In this aspect, as an alternative to the mechanism having a catch, the hinge assembly could include a rotor having at least one end tooth, the rotor angularly communicating with the disk and the proximal and the distal members, where engagement of the lock slide with the at least one end tooth facilitates the dampening of angular displacement in a direction toward flexion and the urging of angular displacement in a direction toward extension. In this aspect having a rotor, the hinge assembly could further include a spring housing having a channel to keep each spring, each spring compressing against walls of the channel to dampen the angular displacement in a direction toward flexion and decompressing from the walls of the channel to urge the angular displacement in a direction toward extension. In this aspect having a rotor, angular displacement of the rotor could cause the rotor to bear against each spring to forcibly compress each spring against the walls of the channel.

In another aspect of the present invention, angular displacement of the proximal member relative to the distal member occurs by rotation about a single pivot point. In this aspect, the disk could be rotatable about the single pivot point to set the first and the second pre-determined ranges. In this aspect, the first pre-determined range could be approximately 90° to 120° about the pivot point, and could occur when the proximal member lies about the pivot point between approximately 60° to 180° relative to the distal member. Further, the second pre-determined range could be approximately 0° to 30° about the pivot point, and could occur when the proximal member lies about the pivot point approximately 150° to 180° relative to the distal member. In this aspect having a single pivot point, the at least one spring could be a torsion spring or an elastomeric spring.

In another aspect of the present invention, a bi-directional damping hinge assembly includes a first member movably connected to a second member to allow angular displacement of the first member relative to the second member in each of extension and flexion (clockwise and counterclockwise positions), where one elastomeric spring communicating with the first and the second members restrains angular displacement in a flexion position, and another elastomeric spring communicating with the first and the second members restrains angular displacement in an extension position. In each direction, the angular movement is dampened through compression of the respective elastomeric spring. After dampening the movement in either direction, returning angular movement is assisted through decompression of the respective elastomeric spring. The elastomeric spring can be adapted to provide a pre-determined force deflection curve in compression and an independent rate of return hysteresis in decompression. The elastomeric springs could be urethane.

In another aspect of a bi-directional embodiment, the elastomer restraints could be provided with set screws in channels to control dorsi and plantar flexion moments. Each set screw could adjust a size of the a respective channel, thereby applying or relieving channel compressing forces on the respective elastomer spring, which thereby adjusts the dampening shock absorption forces provided by the elastomer during further compression, and subsequent assistance forces provided by the elastomer during decompression.

In another aspect of a bi-directional embodiment, the elastomer restraints are configured so that, while one elastomeric spring compresses, another decompresses at the same time, providing a dynamic fine-tuning to the dampening and assistance forces; for example, providing adjustable shock absorption at initial heel contact and through gait with return hysteresis.

In another bi-directional hinge assembly embodiment a first member is movably connected to a second member to allow angular displacement of the first member relative to the second member in each of extension and flexion positions. In this aspect, the hinge assembly also includes at least one elastomeric spring communicating with the first and the second members to restrain angular displacement from an extension to a flexion position, and from a flexion to an extension position, through compression of the at least one elastomeric spring, and to assist angular displacement from a flexion to an extension position, and from an extension to a flexion position, through decompression of the at least one elastomeric spring.

In another aspect of a bi-directional embodiment, angular displacement is restrained over a predetermined angular range in each of the flexion and extension positions from a user selected initial point. Returning angular displacement can be assisted back to the user selected initial point.

Other bi-directional embodiments provide a hinge assembly including a proximal member movably connected to a distal member to allow angular displacement of the proximal member relative to the distal member, two spring housings communicating with the proximal and the distal members, where movement of the spring housings track movement of one or both of the proximal and the distal members. In this embodiment, the hinge assembly could further include a first elastomeric spring in bearing engagement with a respective first spring housing, and a second elastomeric spring in bearing engagement with a respective second spring housing, where angular displacement of the proximal member relative to the distal member from an initial point in a first direction compresses the first elastomeric spring (or both elastomeric springs) to dampen the angular displacement in the first direction, and where decompression of the first elastomeric spring (or both elastomeric springs) urges angular displacement of the proximal member relative to the distal member in a second direction back to the initial point. Further, angular displacement of the proximal member relative to the distal member from the initial point in the second direction could compress the second elastomeric spring (or both elastomeric springs) to dampen the angular displacement in the second direction, and decompression of the second elastomeric spring (or both elastomeric springs) could urge angular displacement of the proximal member relative to the distal member in the first direction back to the initial point. The spring housing can include a channel to keep each elastomeric spring, each elastomeric spring then compressing against inner walls of the channel.

In certain embodiments the hinge assembly could further include a worm gear, and a disk or wheel with worm teeth, the worm gear and the worm teeth being engagably positioned so that operation of the worm gear engages and the worm teeth to lock the proximal member relative to the distal member, thereby setting the bi-directional range of dampening and returning assistance action. This dampening range of motion (ROM) could be any selected range less than 360°, and the worm gear and associated disk with worm teeth could be configured for engagement capability over the 360° range.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings certain embodiments of the present invention. It should be understood, however, that the invention is not limited to the precise arrangements and instrumentalities shown. In the drawings, the same reference numerals are employed for designating the same elements throughout the several figures. In the drawings:

FIG. 3b illustrates an underside, perspective, exploded view of the hinge assembly of FIG. 3a;

FIG. 4b illustrates a back, or underside, perspective, exploded view of the cable release mechanism of FIG. 4a;

FIG. 7b illustrates an underside, perspective, exploded view of the hinge assembly of FIG. 7a;

FIG. 9b illustrates an overhead, or front-side, perspective, exploded view of the hinge assembly of FIG. 9a;

FIGS. 17a through 17l illustrate assembly of, and interaction between, components of the bi-directional knee joint of FIG. 16a.

DETAILED DESCRIPTION OF THE INVENTION

Figure 1:
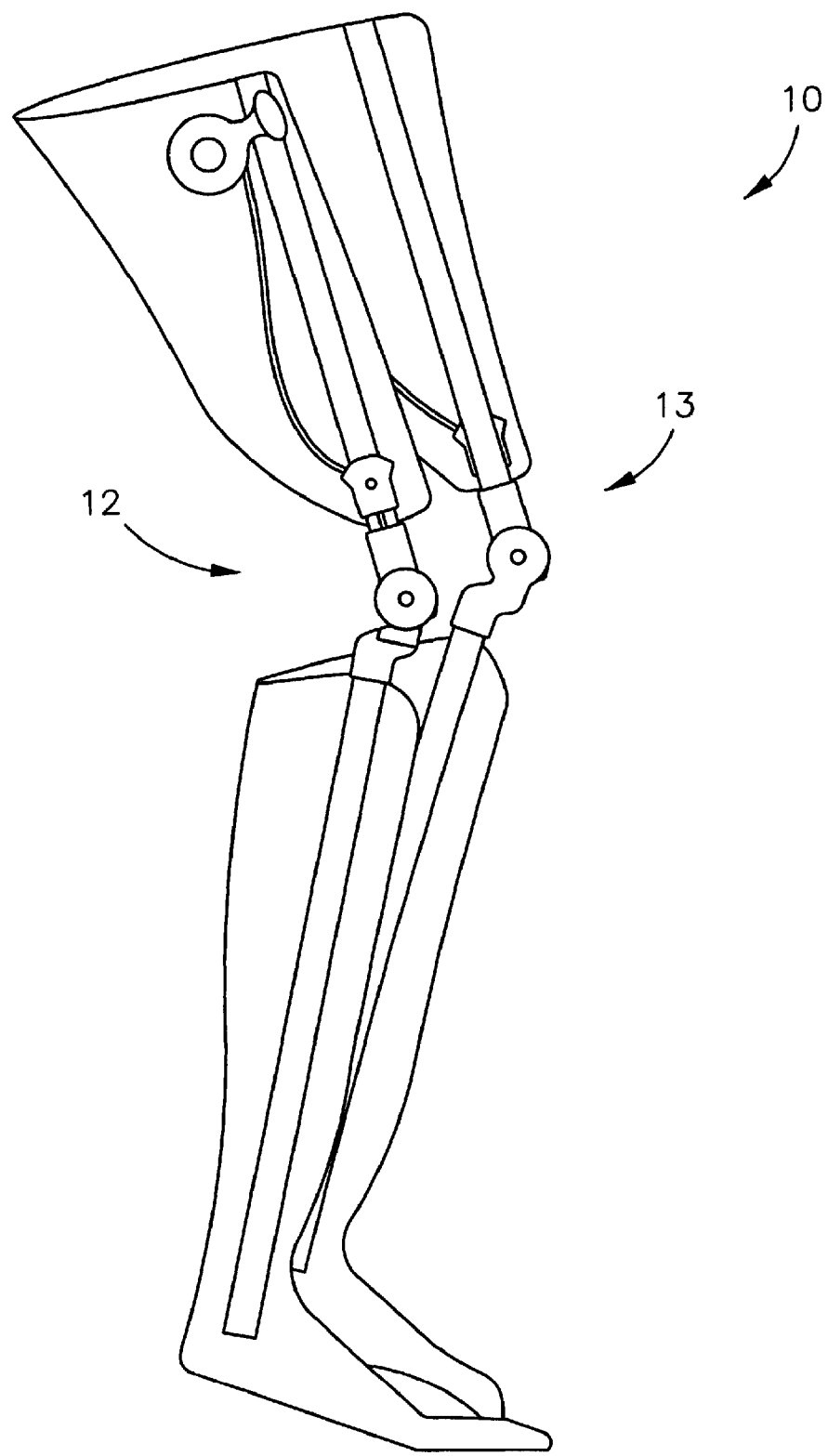
FIG. 1 illustrates an orthotic knee brace for the right leg in accordance with one embodiment of the present invention.

The present invention is a joint or hinge assembly generally, and more particularly an ambulating knee joint having several embodiments, functioning to address various problems while offering advantageous rehabilitative capabilities. Embodiments of the present invention include one or more of the following features:

- dynamic shock absorption at initial contact (i.e. heel strike) to dampen ground reaction forces and loading responses, for smoother knee flexion during gait;
- swing assist to achieve full terminal swing in the presence of extensor weakness, thereby ensuring that the heel hits the ground first (rather than the mid or forefoot);
- sit-to-stand support from a chair, for those having difficulty rising from a sitting position, through a one-way, step-advance ratchet from full flexion (approximately 120° flexion) to full extension, that allows knee extension but prevents knee buckling by locking if the knee begins flexion before reaching a standing position;
- an adjustable range of motion, adjustable between typical flexion angles experienced during stance phase of gait (e.g., between 0-30° in current exemplary use), the adjustable range of motion defining an operating range for the variably controlled knee flexion (without knee locking) and extension during walking or standing through use of a range of motion (ROM) disc adjusted by a worm gear, the ROM disc allowing knee flexion, but also arresting flexion if the knee buckles (e.g., due to weak quadriceps) beyond the set point of the range of motion, arresting flexion thereby preventing a fall;
- an elastomeric spring providing variable force deflection curves to mimic desirable muscle responses, providing variable restraint of flexion and assisting extension at various angles of flexion and extension; and
- a lever lock employing a toggle cam to engage and disengage the sit-to-stand, one-way, step-advance ratchet support, the 0-30° controlled knee flexion/extension with elastomeric spring shock absorption and swing assist, and a release enabling free-rotation (a ROM disc override) for sitting, the lever adapted for easy "pushing" by the knuckles or "raking" by the clawed fingers of an impaired hand (e.g., by stroke), the "pushing" and "raking" requiring little finger force, sensation or dexterity as gross elbow movement is employed, the clawed fingers remaining in a natural resting position, the toggle and cam providing visual, sensory and auditory feedback that the lock is properly engaged or disengaged, the lever assembly being low profile for actuation under clothing. The toggle cam also provides fine adjustment to properly tension cable release for engagement and disengagement.

Exemplary Uses of the Present Invention

The present invention can be used in any joint or hinge assembly, particularly those benefiting from a dampening and/or resisting of two members angularly moving closer to one another, and an urging and/or assisting of the two members angularly extending away from one another. Further, the present application has applicability in any muscle adaptation system, such as in robotics, as the elastomeric spring can be adapted to mimic any bodily tissue and/or musculature. Additionally, any flexible ligamentous joint can be supported and assisted (orthotics), rehabilitated, or replaced (prosthetics) with an adaptation of the present invention.

More particularly, in one embodiment the present invention satisfies the rehabilitation needs of a stroke patient. Stroke patients often suffer a partial, temporary, or permanent paralysis to one side of the body. Accordingly, muscle strength, control, and coordination are reduced. During rehabilitation, the patient is encouraged to walk as much as possible to re-train, control and re-strengthen the muscles, and to stimulate the neuro-plasticity of the brain to re-learn to walk. Patients often lack the necessary confidence and strength to walk without falling; such a patient could be fitted with an orthotic knee brace employing an embodiment of the present invention.

In this embodiment, the joint would likely be set, initially, with a 0° range of motion. As such, the knee is locked in full extension, giving the patient stability in stance, and a confidence that they will not fall due to knee buckling. As rehabilitation progresses some range of motion would be allowed, and then would be incrementally increased as the hinge assembly of the present invention can be adjusted to enable between 0-30° of flexion in infinite degree increments. Incrementally increasing the range of motion during rehabilitation enables a re-development of a normal gait, while still offering support if the knee fails to prevent knee buckling.

In another embodiment, and perhaps in the orthotic embodiment above, an extension moment at the knee assists the limb in the swing-phase of gait, thereby helping the knee reach full extension for muscle reeducation, strengthening, and cortical retraining. This embodiment could further include restraint of flexion, providing dynamic shock absorption at initial contact (i.e. heel strike) to dampen ground reaction forces and loading responses for smoother knee flexion during gait, such as in forced limb use programs, stroke rehabilitation, and in any permanent extensor weakness causing knee instability and buckling.

Other potential uses for the brace include any condition (neurological or orthopedic), which weakened the extensor mechanisms, preventing the patient from reaching full extension during walking or causing knee buckling during stance when the limb bears weight.

The joint can be mounted either on a traditional metal and leather KAFO, or a molded plastic or composite brace. Mounts could accommodate ¾×3/16 or ¾×¼ in aluminum or stainless steel uprights, or some other type of connector to be used with composite or molded brace construction.

An Exemplary Embodiment of the Present Invention

One embodiment of the invention incorporates a hinge assembly into an ambulating knee joint having an elastomeric spring dampening system that cushions weight-bearing shock during walking, dampening flexion, and assists leg extension during the swing-phase of gait. The dampening and swing assist moments operate within a range of motion as provided by a range of motion (ROM) disk and determined by an adjustable worm gear mechanism. In this embodiment, the range of motion can be set between 0° and 30°, adjustable therein depending on the strength and needs of the patient (i.e., as the patient becomes stronger, less support is needed, and the range of motion can usually be increased). The dampening and swing assist forces within this range of motion can also be adjusted to individual needs to sufficiently provide a moment at each swing through phase of gait and to provide shock absorption for smoother walking by redirecting forces toward forward progression to reduce an energy cost of walking for the patient.

Please note that although the following exemplary embodiments illustrate angular displacement of a first, or proximal, member relative to a second, or distal, member about a pivot point, and illustrate angular movement capability of other components (e.g., a disk, a spring assembly) about the same pivot point, the present invention is not limited to such structure. The present invention includes, and features of the present invention are applicable to, hinge assembly angular articulation about instance centers, eccentric surfaces, polycentric and multicentric axes, a plurality of camming surfaces, etc.

Further, the exemplary embodiments detailed below illustrate a dampening of angular displacement, or articulation, in a direction of flexion, and an urging of angular displacement in a direction of extension. The present invention is also not limited to such directional requirements, the present invention contemplating dampening and assisting in any direction. Accordingly, the present invention further includes, and features of the present invention are applicable to, a dampening, restricting, or restraining of angular displacement from a flexion to an extension position, and/or an assisting, or urging, of angular displacement from an extension to a flexion position.

FIG. 1 illustrates an orthotic knee brace 10 adapted for a right leg ("right hand"), the knee brace 10 incorporating one embodiment of the joint or hinge assembly of the present invention. The knee brace 10 includes right hand lateral joint assembly 12 and a right hand medial joint assembly 13. The joint assemblies function similarly, whether right hand lateral, right hand medial, left hand lateral, or left hand medial, the differences simply being orientation of the respective device relative to its position, particularly effected is the orientation of a distal half joint (described below).

Figure 2:
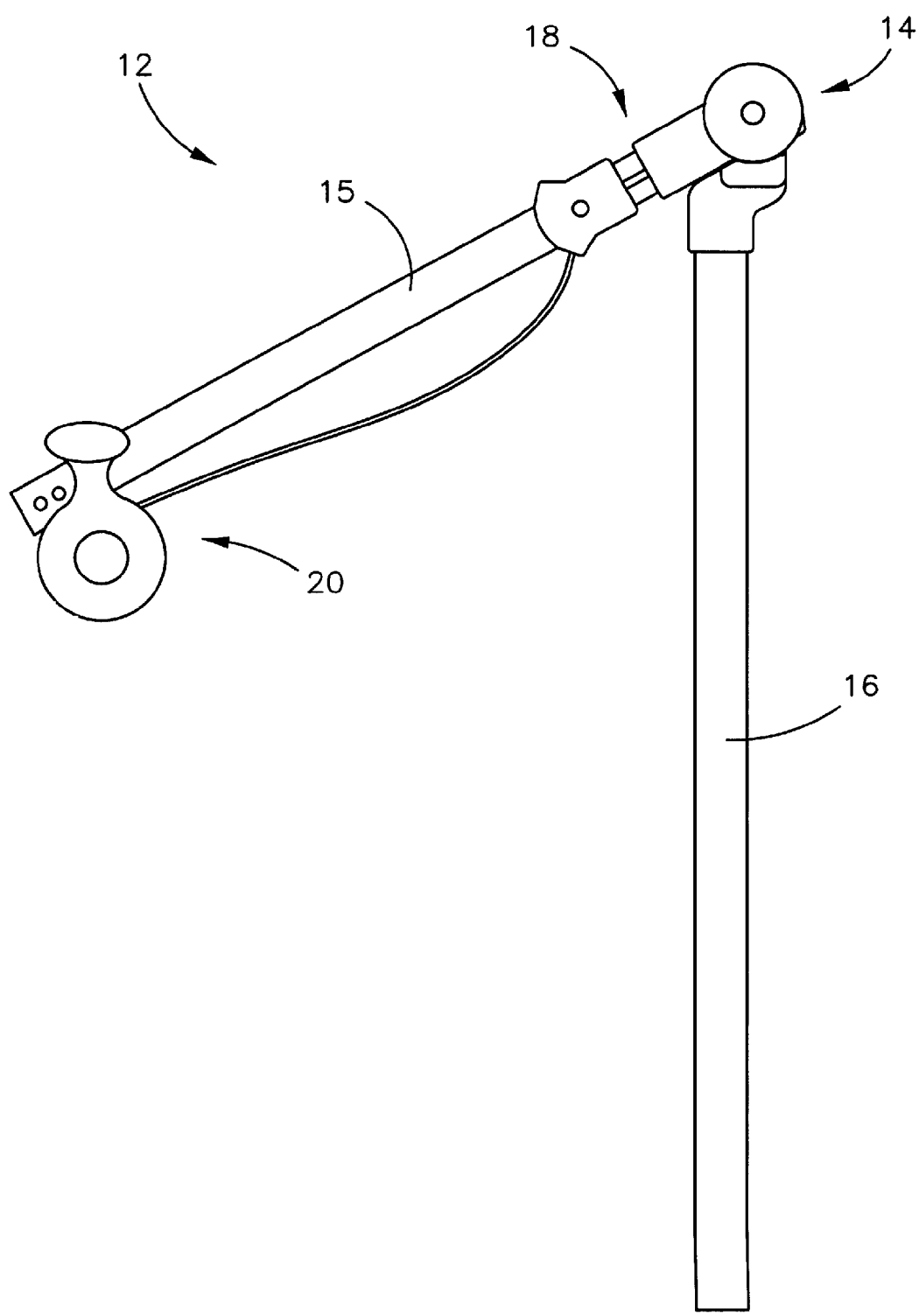
FIG. 2 illustrates a lateral, right-hand hinge assembly with cable release mechanism, and accompanying lateral struts, of the knee brace of FIG. 1.

FIG. 2 illustrates the right hand lateral joint assembly 12 of the orthotic knee brace 10. The joint assembly 12 includes a hinge assembly 14, a proximal strut, or upper member 15, a distal strut, or lower member 16, a lock slide assembly 18 with associated cable release mechanism 20.

Figure 3A:
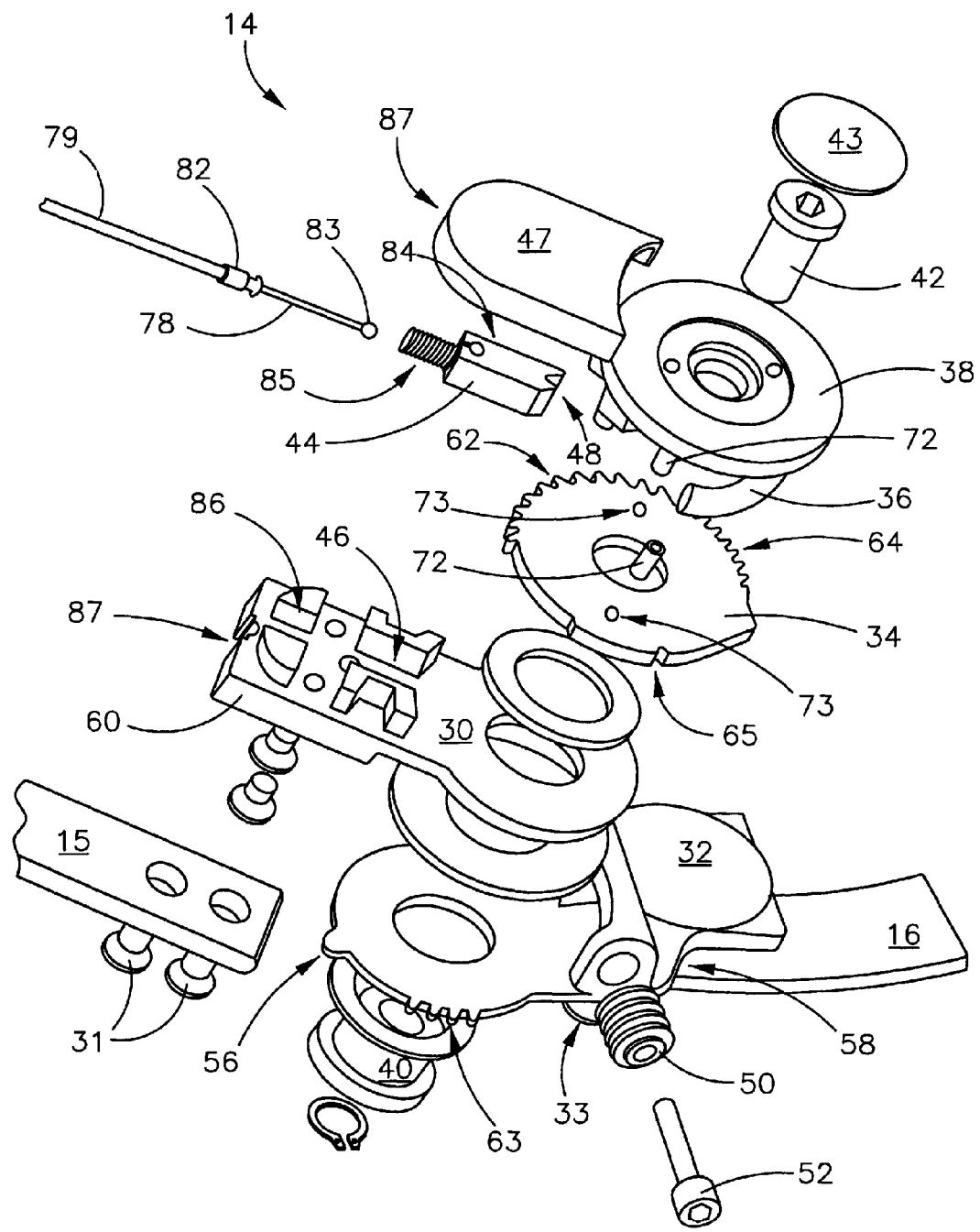
FIG. 3a illustrates an overhead, or front-side, perspective, exploded view of a lateral, left-hand hinge assembly in accordance with one embodiment of the present invention.
Figure 3B:
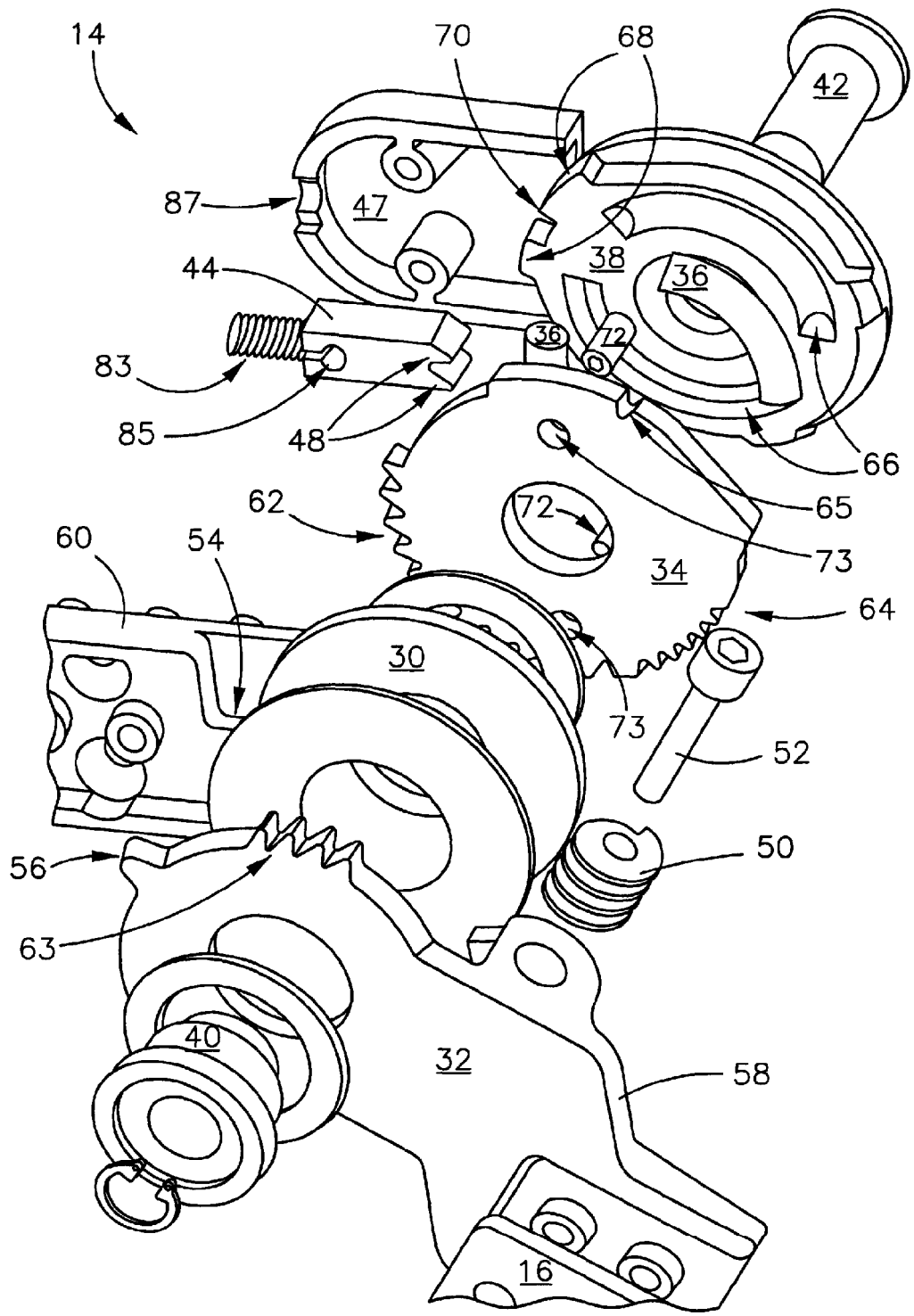

FIGS. 3a and 3b are exploded views of the hinge assembly 14, FIG. 3a being a top, or front side perspective exploded view, FIG. 3b being a bottom, or underside perspective exploded view. Further, the exploded views of FIGS. 3a and 3b actually illustrate a left hand lateral hinge assembly. The hinge assembly 14 includes a proximal half joint 30, fixedly attached to the upper member 15 with screws 31, a distal half joint 32, fixedly attached to the lower member 16 with screws 33, a range of motion (ROM) disk 34, elastomeric springs 36, and a spring housing 38. Certain hinge assembly 14 components are rotatably secured to one another by a pivot post 40 and a break pin 42, with various washers interleaved between the components to facilitate rotational movement, provide wear resistance, remove tolerance build up in thicknesses and length of the pivot post 40 and break pin 42. An aesthetic cover 43 fits within a recess in the spring housing 38 to cover the break pin 42 and access to hinge disassembly.

The proximal half joint 30 houses components of the lock slide assembly 18, the lock slide assembly 18 enabling a rotational step-advance feature when the hinge assembly 14 pivots from a flexion to an extension position. A lock slide 44 is translatably housed within a rectangular recess 46 in the proximal half joint 30 and secured therein by a lock slide cover 47. The lock slide 44 translates linearly within the rectangular recess 46 through a center-line directed toward and through a pivot point of the hinge assembly 14, the pivot point defined by the pivot post 40 and generally by a center of circular portions of the hinge assembly 14 components. The lock slide 44 includes, at its distal end, one or more slide teeth 48.

The distal half joint 32 houses a worm gear 50, rotatably attached to the distal half joint 32 by a worm gear screw 52. The worm gear 50 interlocks with the worm gear screw 52, so that axial rotation of the worm gear screw 52 translates axial rotation to the worm gear 50.

The proximal half joint 30 includes, on its underside, a projecting tab, or stop 54 (the stop lies on a center-line projecting toward the pivot point of the hinge assembly 14). The stop 54 cooperates with a tab 56 radially extending from a perimeter of a circular portion of the distal half joint 32. The stop 54 bears against, or interlocks with, the radially extending tab 56 to prevent hyperextension of the knee when pivoting from a flexion to extension positions (i.e., the stop 54 interlocks with, or bears against, the radially extending tab 56 when the upper member is 180° relative to the lower member). The distal half joint 32 includes an angled shoulder 58 that aligns with, and bears against, a rear edge 60 of the proximal half joint 30, serving as a stop to rotational movement in a flexion direction, and thereby defining a maximum extent of flexion for the hinge assembly 14, occurring when approximately 60° exists between the upper and the lower members 15, 16.

Figure 6A:
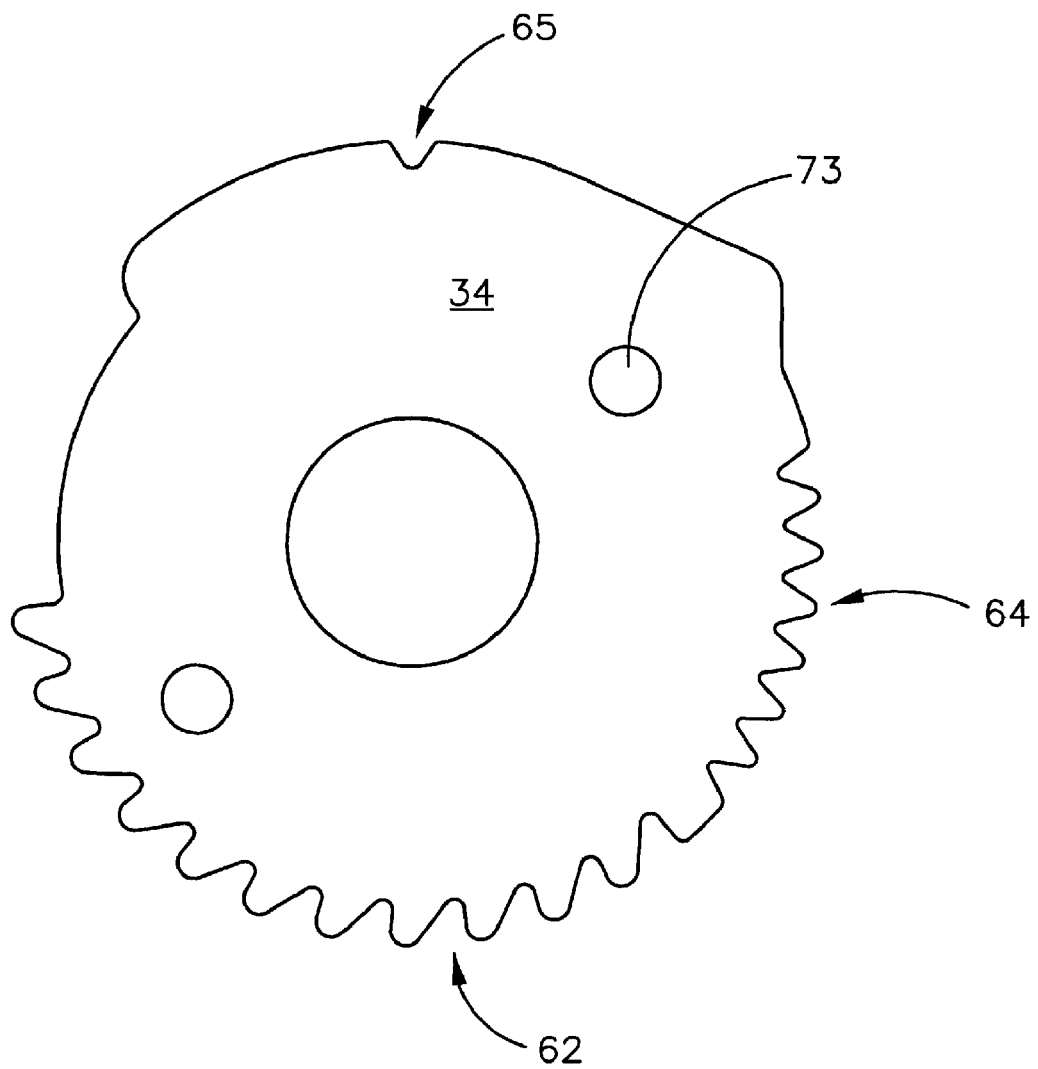
FIG. 6a illustrates the ROM disk of the previous figures, showing worm teeth and the spur teeth located about a perimeter of the ROM disk in a similar plane, FIG. 6a also showing two holes adapted to accept the spring posts.

The ROM disk 34 includes a plurality of spur teeth 62 and a plurality of worm teeth 64 about its perimeter, each lying in a similar plane. The spur teeth 62 each geometrically complement, and are selectably engagable with, the one or more slide teeth 48. Engagement of the spur teeth 62 with the slide teeth 48 work to interlock the lock slide 44 with the ROM disk 34 to arrest rotational motion of the lower member 16 relative to the upper member 15 in a direction of flexion, and enables a one-way step-advance ratcheting in a direction from flexion to extension. The spur teeth 62 are raked, or inclined, as specifically shown in FIG. 6a, to geometrically hold the interlocked spur teeth 62 and the slide teeth 48 together upon knee buckling, as when a user falls back. The weight of a user falling back, causing rotation toward flexion, ramps the spur teeth 62 and the slide teeth 48 together. Due to the incline of the respective teeth, the weight of the user acts to further interlock the geometrically complementing teeth due to the angle of incline.

The worm teeth 64 are engagably positioned with the worm gear 50 so that operation of the worm gear 50 (turning the worm gear 50 about its longitudinal axis) incrementally engages worm teeth 64 to rotate the ROM disk 34 about its axis, thereby adjusting a range of motion upon which the elastomeric spring dampening system will operate to cushion weight-bearing shock during walking and to assist leg extension during the swing phase of gait. In this embodiment, the range of motion is adjustable between approximately 0-30° about the pivot post 40.

The distal half joint 32 further includes indicating teeth 63 which cooperate with a recess 65 in the ROM disk 34 to provide simple indication of the range of motion set by operation of the worm gear 50. As the ROM disk 34 rotates about the pivot post 40, by operation of the worm gear 50, to adjust the range of motion, adjacent alignment of the recess 65 with a certain indicating tooth 63 would provide indication of a certain degree of range of motion set. For instance, in the embodiment shown in FIGS. 3a and 3b, each of four indicating teeth 63 would indicate a 100 change in range of motion (i.e., 0°, 10°, 20°, 30°). This feature is helpful to ensuring that the range of motion set for a lateral hinge assembly 12, for instance, is the same as that set for a corresponding medial hinge assembly 13.

The spring housing 38 includes two convex, cylindrically shaped channels 66, each channel 66 housing an elastomeric spring 36. In this embodiment, each elastomeric spring 36 is a cylinder of urethane. However, other elastomeric materials can be employed, such as but not limited to silicon, silicone urethane, nylon, and delrine. Depending on the dampening and urging application, various elastomeric materials, with properties ranging from elastic to inelastic, having varying degrees of rate of return to original shape or hysteresis, might be desired. The urethane springs can each be selectively designed, in size, shape and composition, to provide a predetermined force deflection curve to match desired shock absorption characteristics, and/or to provide a pre-determined hysteresis to alter the rate of return of the elastomeric material to original (i.e., at rest, or no load) shape, to match desired swing assist and cadence characteristics, as discussed below.

Figure 5A:
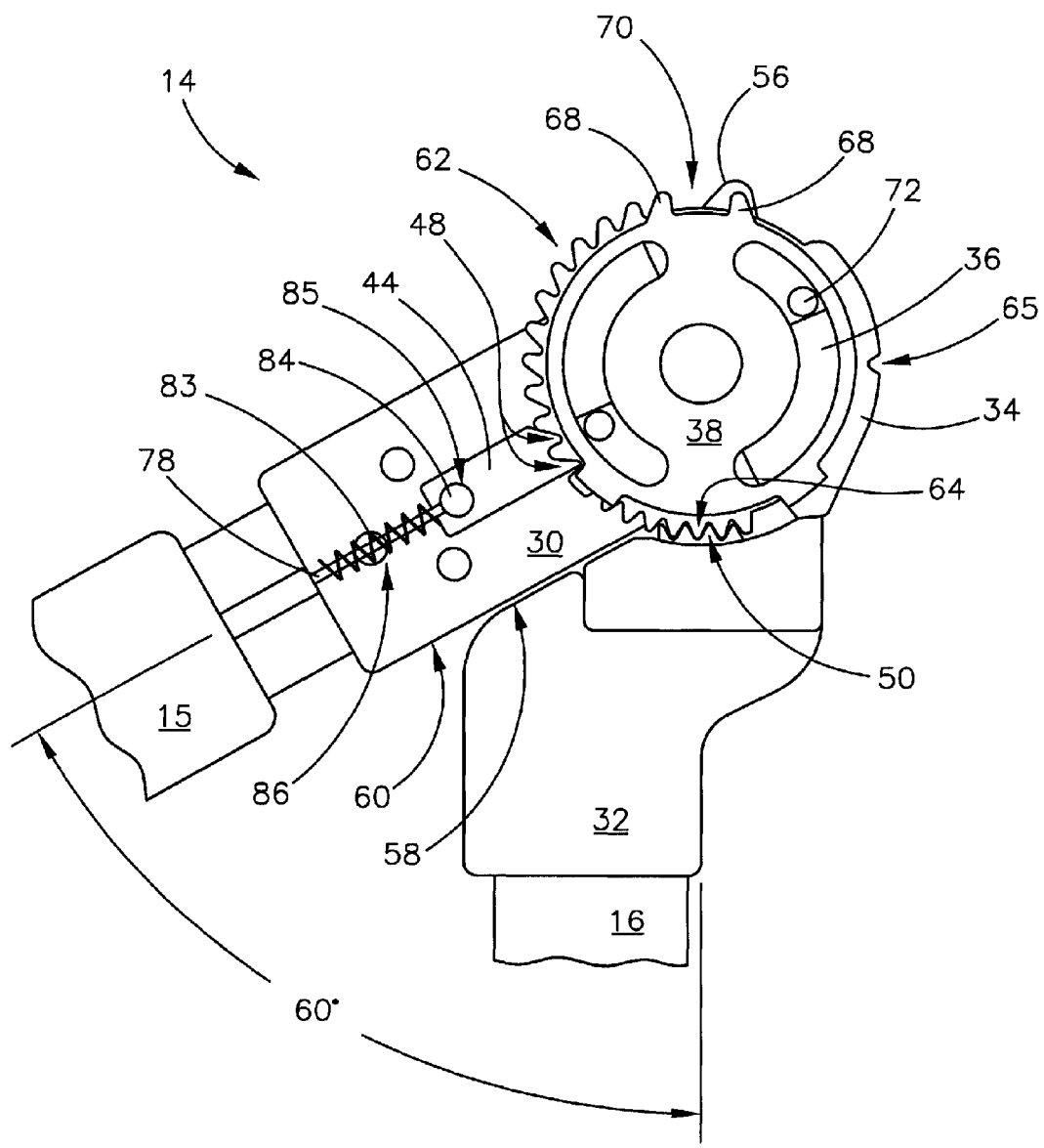
FIG. 5a illustrates a front elevation view of the hinge assembly of FIG. 1 in a position of full flexion, with slide teeth of a lock slide engaging spur teeth of a range of motion (ROM) disk to provide one-way, step advance ratcheting of rotational movement toward extension, FIG. 5a also illustrating the ROM disk set for a 30° range of motion, with elastomeric springs partially compressed (providing pre-load) due to spring post positioning within respective channels.

The spring housing 38 includes two radially extending tabs 68, forming a catch 70 therebetween to receive the lock slide 44 upon full extension of the hinge assembly 14, thereby enabling dampening upon subsequent flexion of the hinge assembly 14, and enabling assistance upon extension. The ROM disk 34 includes two spring manipulating posts 72, each housed within a post hole 73 in, and perpendicularly extending from an outer face of, the ROM disk 34. Each spring post 72 is positioned for reception by one of the channels 66 of the spring housing 38, as shown in FIG. 5a, and for bearing engagement with an end of a respective elastomeric spring 36. When the lock slide 44 is secured within the catch 70, the spring housing 38 becomes rotatable relative to the ROM disk 34, so that a subsequent flexion of the hinge assembly 14 causes each spring post 72 to compress a respective elastomeric spring 36 within the respective channel 66, and against the channel 66 and the ROM disk 34. As flexion of the hinge assembly 14 increases (i.e., the upper member 15 moves toward the lower member 16), the portion of the channel 66 housing the respective elastomeric spring 36 decreases in area (due to spring housing 38 movement relative to the spring post 72), causing ever increasing confinement of the respective elastomeric spring 36. The elastomeric springs 36, during compression, provide resistance to, or dampening of, flexion of the hinge assembly 14, thereby providing the shock absorption feature of the knee brace 10 upon heel strike and weight bearing transfer during walking. Consequently, removal of weight from the flexed limb results in a decompressive force of the elastomeric springs 38 upon the spring posts 72 of the spring housing 38, which thereby urges, or assists, knee movement during the swing phase of gait from a flexion to an extension position. When the lock slide 44 is not secured within the catch 70, the flexion restraint and extension assistance features are disengaged, as rotatable movement of the spring housing 38 relative to the ROM disk 34 is avoided.

Figure 4A:
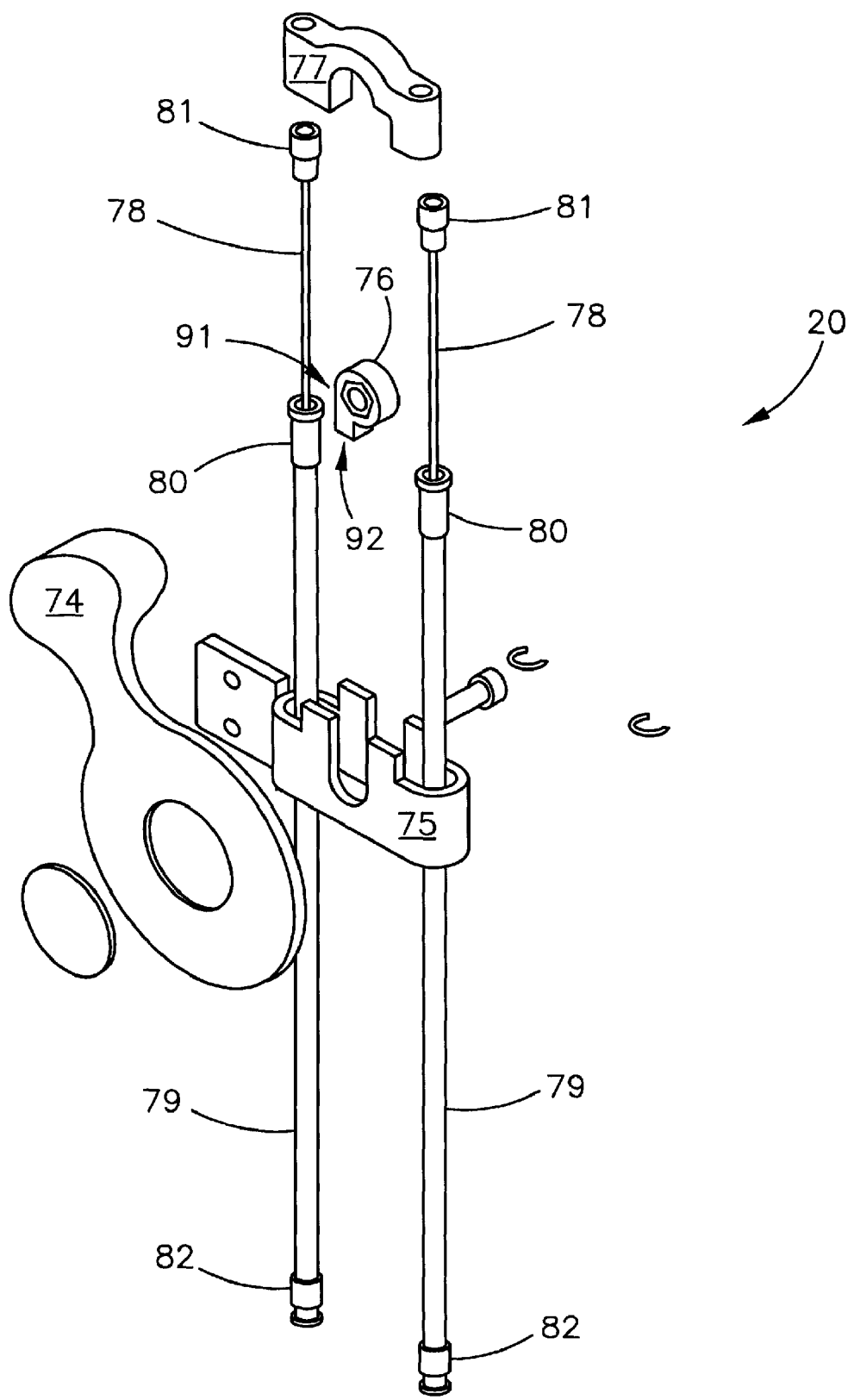
FIG. 4a illustrates a front-side, perspective, exploded view of a cable release mechanism in accordance with one embodiment of the present invention.
Figure 4B:
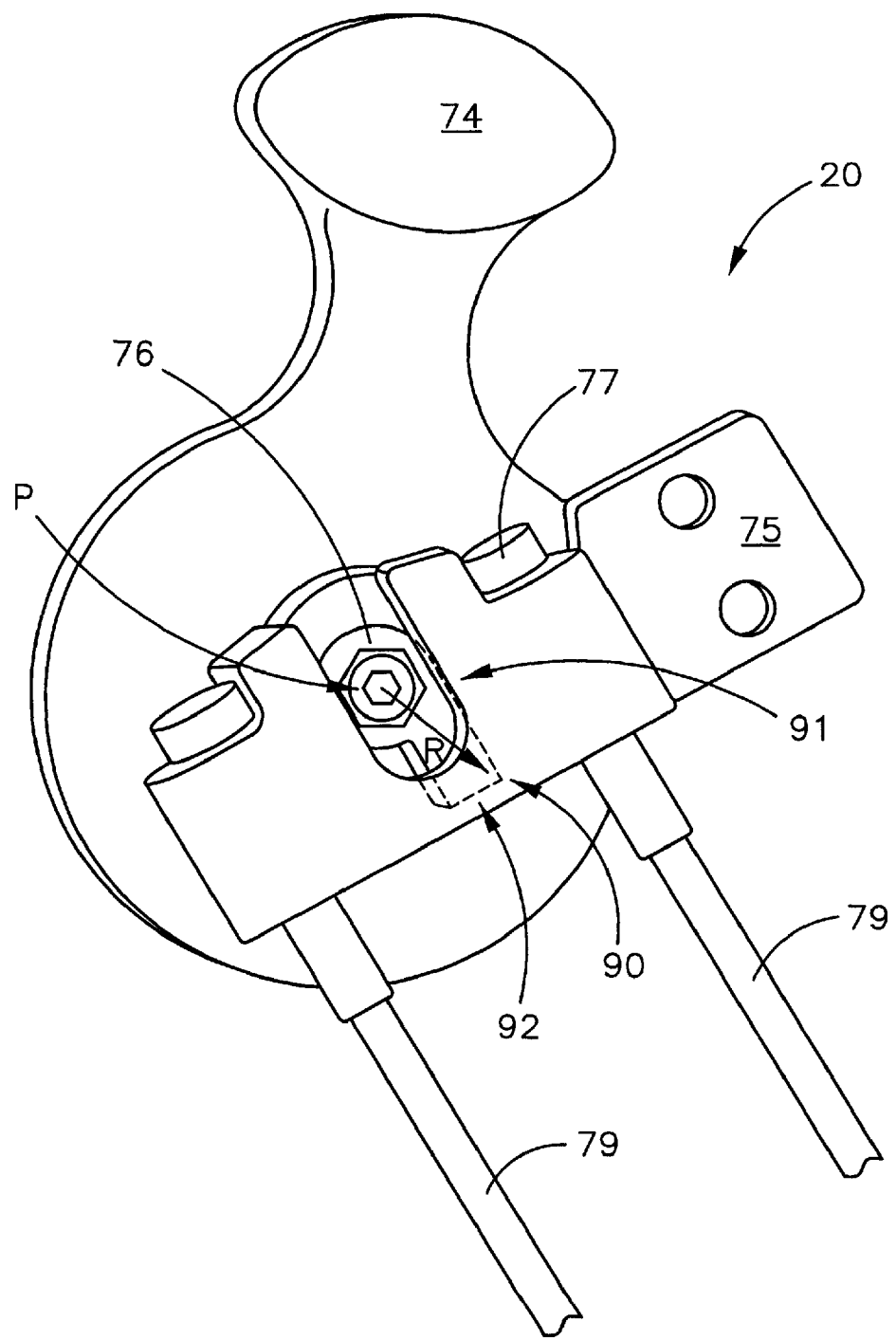

Referring now to FIGS. 4a and 4b, the cable release mechanism 20 of associated lock slide assembly 18 includes a lever 74, a cable release housing 75, a toggle cam 76, a cable slide 77, and two cables 78. The two cables 78 are each retained within a tube 79, each tube 79 having on its proximal end a housing fitting 80 which cooperates with a threaded terminal 81 on each cable 78 end to retain the cable slide 77 within a recess in the housing 75. Each of the two cables 78 operate a respective lock slide assembly 18 (one serving the lateral joint assembly 12 and the other serving the medial joint assembly 13).

Referring now to FIGS. 3a, 4a, and 4b, each tube 79 has on its distal end a lock slide end fitting 82 which cooperates with the proximal half joint 30 to terminate the cable release mechanism 20 at the lock slide assembly 18. A bulbous cable fitting 83, at a distal end of the cable 78, resides within a circular recess 84 in the lock slide 44. The cable 78 passes through the distal biasing spring 85 residing within a spring recess 86 in the proximal half joint 30. The lock slide end fitting 82 is nestled and secured within a detent 87 formed within the proximal half joint 30 and the lock slide cover 48 upon attachment of the lock slide cover 48 to the proximal half joint 30. The distal biasing spring 85 predisposes the slide teeth 48 of the lock slide 44 into engagement with the spur teeth 62 of the ROM disk 34, or predisposes the lock slide 44 into engagement with the catch 70 of the spring housing 38, depending on the position (flexion or extension) of the lower member 16 (or distal half joint 32) relative to the upper member 15 (or proximal half joint 30). Pulling the cables 78 compresses the distal biasing spring 85 and retracts the lock slide 44, thereby translating the lock slide 44 away from the pivot point and disengaging the lock slide 44 from either the spur teeth 62 of the ROM disk 34 or the catch 70 of the spring housing 38. When the lock slide 44 is disengaged from the spring housing 38 and the ROM disk 34, the lower member 16 rotates freely relative to the upper member 15 about the pivot point within a range of approximately 120°.

Referring now to FIGS. 2, 4a, and 4b, at a proximal end of the upper member 15, the cable release housing 75 is fixedly attached to the upper member with setscrews. The lever 74 is fixedly secured to the toggle cam 76 by retaining screw 88. The toggle cam 76 is rotatably and translatably housed within the recess in the cable release housing 75, being retained therein by the cable slide 77 biased to retain the toggle cam 76 within the housing 75 by taut cables 78.

The toggle cam 76 is designed with a projecting cammed surface 90, a first flat surface 91, and a second flat surface 92, the cammed surface 90 bearing against a bottom 75 of the recess in the cable release housing 75. When the lever 74 is pivoted about the retaining screw 88 (at pivot point "P"). The projecting cammed surface 90, bearing against the bottom 75 of the recess in the cable release housing 75, causes the retaining screw 88 and cable slide 77 to translate linearly within the recess of the cable release housing 75 a sufficient distance so that the cables 78 retract the respective lock slides 44, disengaging the lock slides 44 from the respective spring housings 38 or ROM disks 34 of the medial and the lateral hinge assemblies 14. The projecting cammed surface 90 incorporates a radius "R" (relative to the pivot point P) greater than that of distances to either of the first or the second flat surfaces 91, 92, which causes a toggle action and snap, under cable tension, when moving from a cammed surface 90 engagement with the bottom 93 to either a first or a second flat surface 91, 92 engagement with the bottom 93, thereby providing a user with a positive and certain positioning (engagement or disengagement) of the lock slide assembly 18 for each of the lateral and medial joint assemblies 12, 13.

Accordingly, each cable 78, when positioned in retraction, independently exerts a force greater than that of the corresponding distal biasing spring 85 to assure a force necessary to fully disengage the lock slide 44. The toggle cam 76, due to the cammed surface 90, linearly translates the cables 78 a distance greater than that necessary to disengage the lock slide 44 from each hinge assembly 14, and does so without over-tensioning the respective cable 78. Additional components that can be employed to assist in preventing cable over-tensioning are detailed later in a description of another embodiment of a cable release mechanism.

When the lever 74 is "raked" up (as shown in FIGS. 4a and 4b), the second flat surface 92 (with distance to the pivot point P greater than that of the first flat surface 91) is adapted to hold the cable in a "proximally pulled" position to hold the lock slide 44 in a fully disengaged position relative to the ROM disk 34 and the spring housing 38. When the lever 74 is "knuckled" down, relative to the patient, the first flat surface 91 (with distance to the pivot point P less than that of the second flat surface 92) is adapted to enable a more distal positioning of the tensioned cables 78, permitting the lock slide 44 to remain in a fully engaged position relative to the ROM disk 34 or the spring housing 38.

An Operating Description of the First Exemplary Embodiment

FIGS. 5a-5e illustrate the hinge assembly 14 of the knee brace 10 in various positions of use, each position employing one or more features of the present invention. FIG. 5a illustrates the hinge assembly 14 in a position of full flexion, with the angled shoulder 58 of the distal half joint 32 bearing against the rear edge 60 of the proximal half joint 30, the bearing relationship serving as a stop to rotational movement in a flexion direction. At full flexion, approximately 60° exist between the upper and the lower members 15, 16. Accordingly, approximately 120° defines a complete range of motion between full flexion and full extension.

FIG. 5a shows the lock slide 44 engaging respective spur teeth 62 of the ROM disk 34, thereby enabling sit-to-stand support, for users having difficulty rising from a sitting position, through one-way, step-advance ratcheting. As shown in FIG. 5a, rotational movement toward extension causes the slide teeth 48 to incrementally advance, and ratchet, over the spur teeth 62 of the ROM disk 34. This one-way, step advance ratcheting allows controlled knee extension while preventing knee buckling. If a knee begins a flexing movement (i.e., begins buckling) before reaching full extension, the slide teeth 48 engage with and lock into the spur teeth 62. Upon full extension, the slide teeth 48 disengage from, and move out of the vicinity of, the spur teeth 62.

Figure 5B:
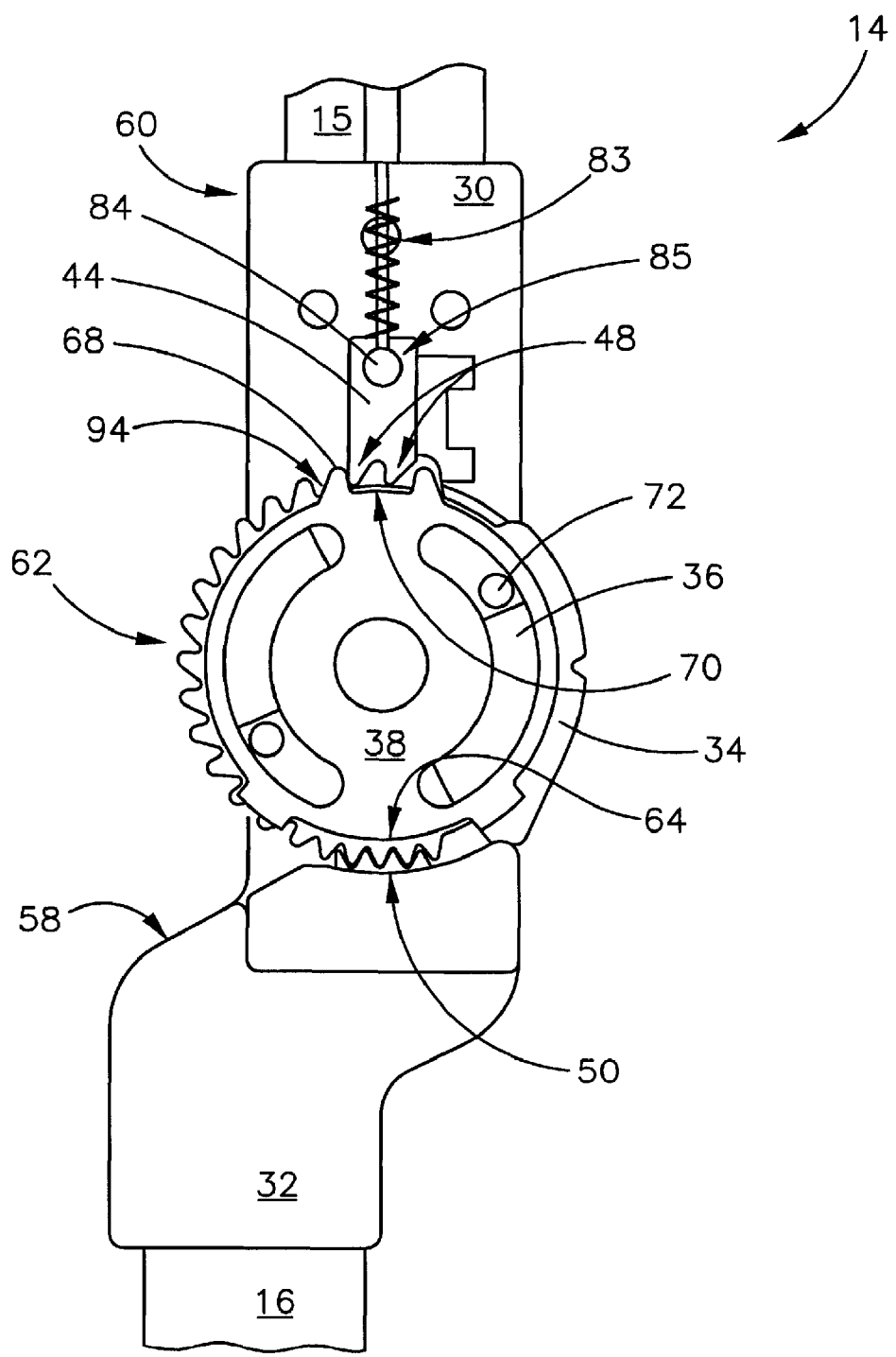
FIG. 5b illustrates a front elevation view of the hinge assembly of FIG. 1 in a position of full extension, with the slide teeth engaging a catch in a spring housing and the ROM disk set for a 0° range of motion (i.e., the slide teeth abut a proximal most spur tooth of the ROM disk, the abutment arresting rotational movement toward flexion)

FIG. 5b illustrates the hinge assembly 14 in a position of full extension, with the lock slide 44 secured within the catch 70 of the spring housing 38. Although engaged within the catch 70, the lock slide 44 (as shown in FIG. 5b) still abuts a proximal most spur tooth 94 located about a perimeter of the ROM disk 34. The proximal most spur tooth 94 is shown in FIG. 5b partially behind a rearmost radially extending tab 68 (rearmost because FIG. 5b is a view of a right handed, lateral hinge assembly 14). In this position, at least one slide tooth 48 of the lock slide 44 will bear against the proximal most spur tooth 94 during any attempted movement toward flexion. The hinge assembly 14, therefore, is locked at full extension. Accordingly, FIG. 5b shows the ROM disk 34 positioned to allow a 0° range of motion, the range of motion being by operation of the worm gear 50. As such, the knee is locked at full extension, giving the user stability in stance, a confidence of not falling due to knee buckling, but requiring the user to walk with a stiff knee and consequential strutting gait. A 0° range of motion might be used by a stroke patient during early stages of rehabilitation, when confidence and strength may be lacking.

Figure 5C:
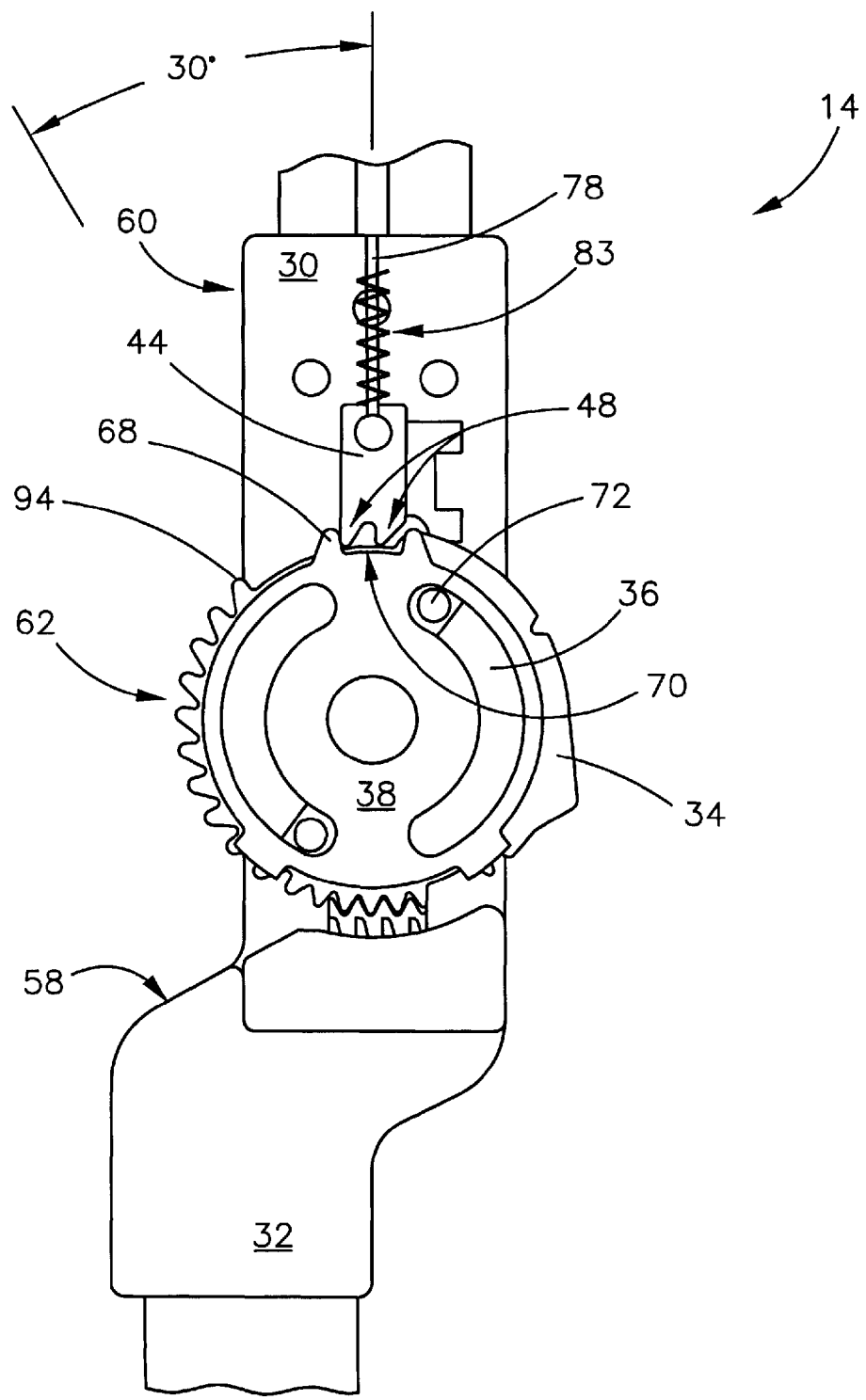
FIG. 5c illustrates a front elevation view of the hinge assembly of FIG. 1 in a position of full extension, with the slide teeth engaging the catch in the spring housing and the ROM disk set for a 30° range of motion, thereby enabling, within the 30° range of motion, a dampening of rotation toward flexion and an urging of rotation toward extension.

FIG. 5c illustrates the hinge assembly 14 in a position of full extension, the lock slide 44 secured within the catch 70 of the spring housing 38, and the ROM disk 34 positioned to allow a 30° range of motion, as set by operation of the worm gear 50, and as shown by the locational relationship between the proximal most spur tooth 94 and the rearmost radially extending tab 68. Within the 30° range of motion, with the lock slide 44 secured within the catch 70, movement toward flexion causes the spring housing 38 to rotate in conjunction with the proximal half joint 30, about the pivot post 40, and to rotate relative to the ROM disk 34 so that each spring post 72, during movement toward flexion, compresses a respective elastomeric spring 36 within and against the respective channel 66 and against the ROM disk 34.

Figure 5D:
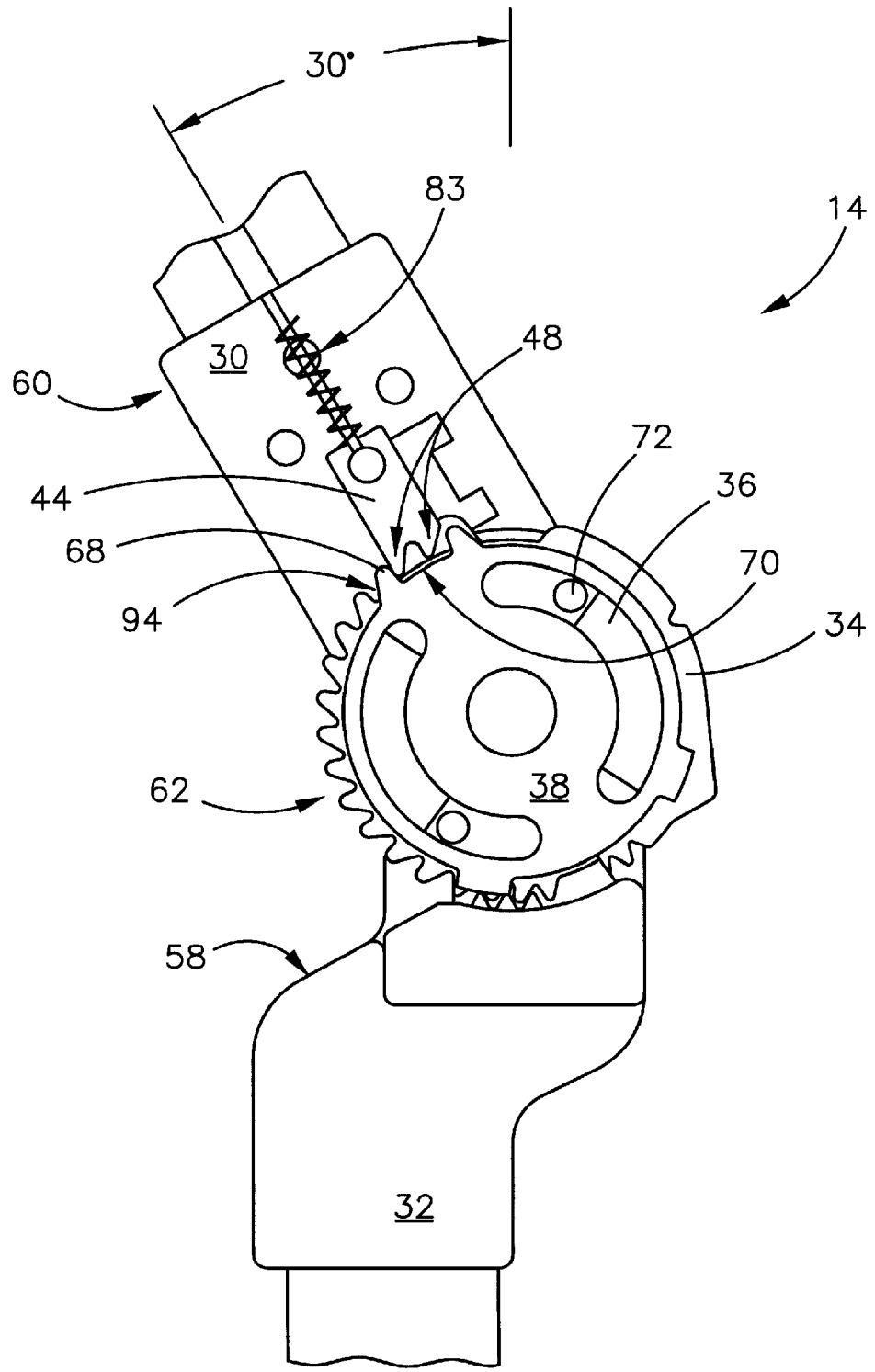
FIG. 5d illustrates a front elevation view of the hinge assembly of FIG. 1 in a position maximizing the 30° range of motion, FIG. 5d showing springs compressed and dampening the rotation toward flexion.

FIG. 5d illustrates the hinge assembly 14 with the lock slide 44 secured within the catch 70, the ROM disk 34 positioned to allow a 30° range of motion, and the elastomeric spring 36 flexion dampening/extension assisting mechanism engaged. FIG. 5d shows the hinge assembly 14 reaching a maximum point within the 30° range of motion, at which point the lock slide 44 will abut the proximal most spur tooth 94 to arrest further flexion, and thereby prevent knee buckling and a possible fall if the user's knee were to fail. FIG. 5d shows the elastomeric springs 36 compressed within respective channels 66 to restrain flexion, to provide dynamic shock absorption at initial contact (i.e. at heel strike through midstance), and to dampen ground reaction forces and loading responses to redirect forces to propel forward progression for greater efficiency for smoother knee flexion during gait. Thereafter, a release of weight bearing force to the hinge assembly 14 causes the compressed elastomeric springs 36 to urge the upper and the lower members 15, 16 back toward extension, thereby assisting the user in achieving full terminal swing in the presence of extensor weakness, and to ensure that the heel hits the ground first (rather than the mid or forefoot) at initial strike. The elastomeric springs 36 can be varied in size, type, and shape, as discussed below, to provide a wide range of force deflection curves, thereby allowing the present invention to mimic a wide variety of desirable muscle responses, and/or to provide varying restraint of flexion and assistance to extension at different points along the range of motion.

Figure 5E:
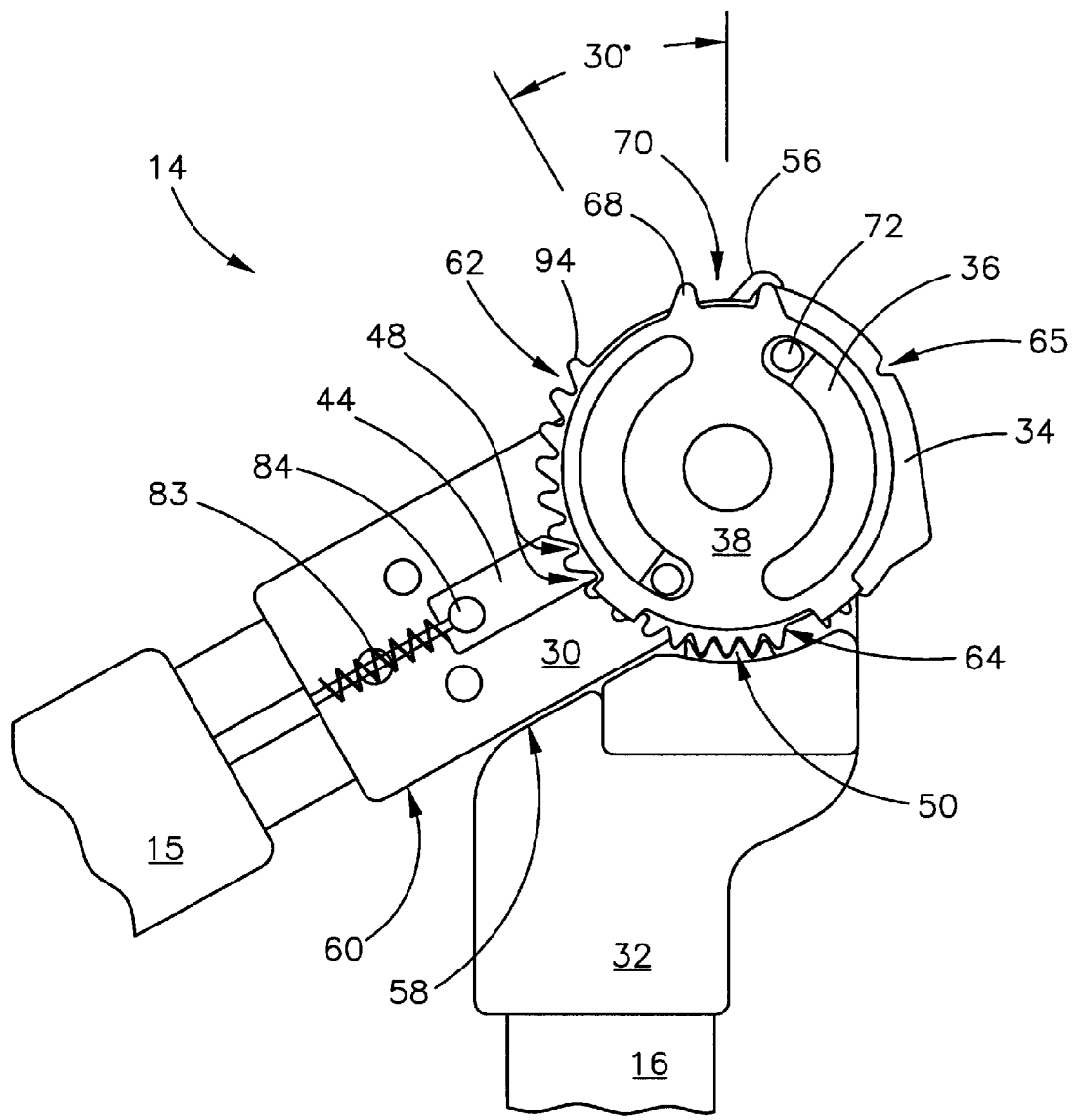
FIG. 5e illustrates a front elevation view of the hinge assembly of FIG. 1 in a position of full flexion, with the slide teeth again engaging the spur teeth to provide one-way, step advance ratcheting of rotational movement toward extension, FIG. 5e also illustrating the ROM disk set for a 30° range of motion, with elastomeric springs at rest (no pre-load) due to spring post positioning within the respective channels.

At any point during operation, proximally translating the cable 78 (i.e., "raking" up the lever 74) disengages the lock slide 44 from the spring housing 38 to allow free rotation of the upper member 15 relative to the lower member 16. Disengaging the lock slide 44 permits flexion beyond the 30° range of motion, to a desired sitting position, up to and including a position of full flexion. At full flexion, "knuckling" the lever 74 down again engages the lock slide 44 with the ROM disk 34 to again enable the one-way step advance feature, as shown in FIG. 5e. FIG. 5e further shows the ROM disk 34 positioned to allow a 30° range of motion, and the elastomeric springs 36 relaxed, with the flexion dampening/extension assisting mechanism disengaged.

Exemplary Embodiments of the Elastomeric Springs

The elastomeric springs 36 are compressed within the channels 66 by the spring posts 72 of the ROM disk 34. The spring posts 72 move within the channels 66, each bearing against one end of an elastomeric spring 36, to translate a non-linear compressing force through the spring 36 beginning at the end. Upon compression, the elastomeric cylinders decrease in length and expand in diameter to frictionally embrace the inner walls of the channels 66 and an outer face of the ROM disk 34. Accordingly, varying the properties of the elastomeric springs 36, and/or varying the characteristics of the frictional embrace of the springs 36 to the channels 66 and the ROM disk 34, can control the force deflection and rate of return response of the elastomeric spring 36.

In one embodiment, the outer diameter of the elastomeric springs is less, or slightly less, than an inner diameter of the channels. In this embodiment, a shape of the inner walls could approximate an exterior of the springs, or could vary to some degree, depending on a deflection response desired. In either case, in this embodiment, the spring diameter must expand to some degree, through compression of length, before the spring will frictionally embrace the inner walls of the channel and the ROM disk. In another embodiment, the outer diameter of the spring might be substantially equal (in shape and diameter) to the inner wall of the channel, thereby creating a higher coefficient of friction to immediately absorb more energy.

In another embodiment, the elastomeric spring might have a hole bored longitudinally therethrough, the hole affecting expansion of the spring diameter during compression, as the spring material must now expand to fill the hole, the hole thereby consequently affecting the coefficient of friction of the spring. The longitudinal hole, and a varying of the diameter of the hole, could be used with either of the spring diameter configurations described above.

In another embodiment, a setscrew or pin is placed in a pre-determined location within the channels to stiffen the dampening response. Since a channel with less surface area (as determined by a position of the setscrew or pin) provides the elastomeric spring less room to expand, the elastomeric spring will become uncompressible sooner, thereby increasing resistance to flexion.

Figure 6B:
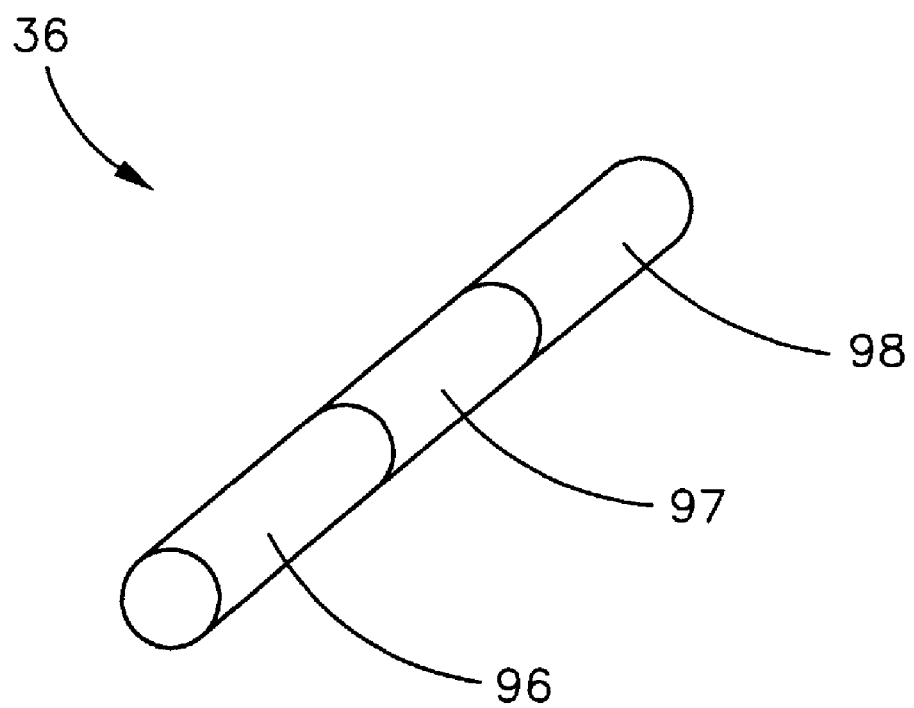
FIG. 6b illustrates one embodiment of an elastomeric spring in accordance with the present invention.

In another embodiment, the cylindrical elastomeric spring 36 is longitudinally segmented with portions of differing durameters, or densities, to vary the restraining force and rate of return over the range of motion of the hinge assembly. Referring now to FIG. 6b, an elastomeric spring 36 is illustrated having three segments, each segment having a different density to impart a certain desired force deflection curve over a respective portion of the range of motion. For example, a first segment 96 may have a relatively low durameter, with corresponding high elasticity, thereby providing a light moment of lesser shock absorption, but providing a rate of return, or extension assistance, typical of a normal swing of gait. The second segment 97 may be of moderate durameter, with corresponding moderate elasticity, thereby providing a greater restraining force and shock absorption, but providing a lesser rate of return. The third segment 98 might include dense material, of high durameter and low elasticity, thereby enabling absorption of greater force, but providing a slower return and consequently not providing a lot of swing assist.

In the above-segmented embodiment of the elastomeric spring 96, the first segment 96, due to its position bearing against the spring post 72, is the first to operate, or acquire compressive forces, during flexion restraint, and the last to operate, or decompress, during extension assistance. For this reason, a material with high elasticity and low durameter may be desirable, to ensure a certain degree of flexion during heel strike and loading response, while providing a high rate of return, or swing assist, to ensure proper heel strike (i.e., to ensure that the heels strikes the ground first) over the final portion, or range, of swing. Since the third segment 98 is the last portion of the elastomeric spring 36 to sustain compressive forces, and offer flexion restraint, over the range of motion during flexion, it may also be desirable to design the third segment 98 of dense material, with high durameter, to provide a high level of shock absorption, or flexion restraint, over this final portion of flexion to avoid a "maxing out" of the joint assembly (i.e., to avoid a complete arresting of flexion upon reaching the maximum range of motion set point (e.g., 30°)) during heel strike and weight transfer.

The hysteresis characteristic of elastomeric materials makes elastomeric materials favorable for employment in the present invention. With elastomeric materials, greater shock absorption, or flexion restraint, in compression does not necessarily result in an equally great rate of return, or swing assist, in decompression. Elastomeric materials return slower, in decompression, than correspondingly respond to a force in compression. This characteristic resembles bodily musculature, where, for instance, a quadricep during heel strike and stance absorbs, or resists, a greater force than the quadricep subsequently returns during the swing phase of gait. This feature makes elastomeric springs advantageous to torsion springs, which return quickly, where a spring loaded to absorb a significant force will subsequently return with swing assist far exceeding that needed or desired by a user. Accordingly, a time rate of compression of an elastomeric spring in response to a certain force is faster than a subsequent time rate of decompression of the elastomeric spring resulting from the certain force. Further, as a result, an elastomeric spring of the present invention can be adapted to provide a pre-determined force deflection curve in compression, and an independent rate of return hysteresis in decompression.

The above-referenced alternatives and aspects of the elastomeric springs provide many characteristic permutations, the various permutations enabling the achievement of myriad force deflection and hysteresis curves. Accordingly, any bodily tissue or muscle can be reproduced, or mimicked, by the present invention. For instance, muscle performance can be assessed in a laboratory, and a force deflection curve charted. Then, an elastomeric spring can be adapted to mimic the charted force deflection curve by selectively determining the necessary size, shape, features, and characteristics of the elastomeric spring.

Alternative Embodiments of the Hinge Assembly and Cable Release Mechanism

Figure 7A:
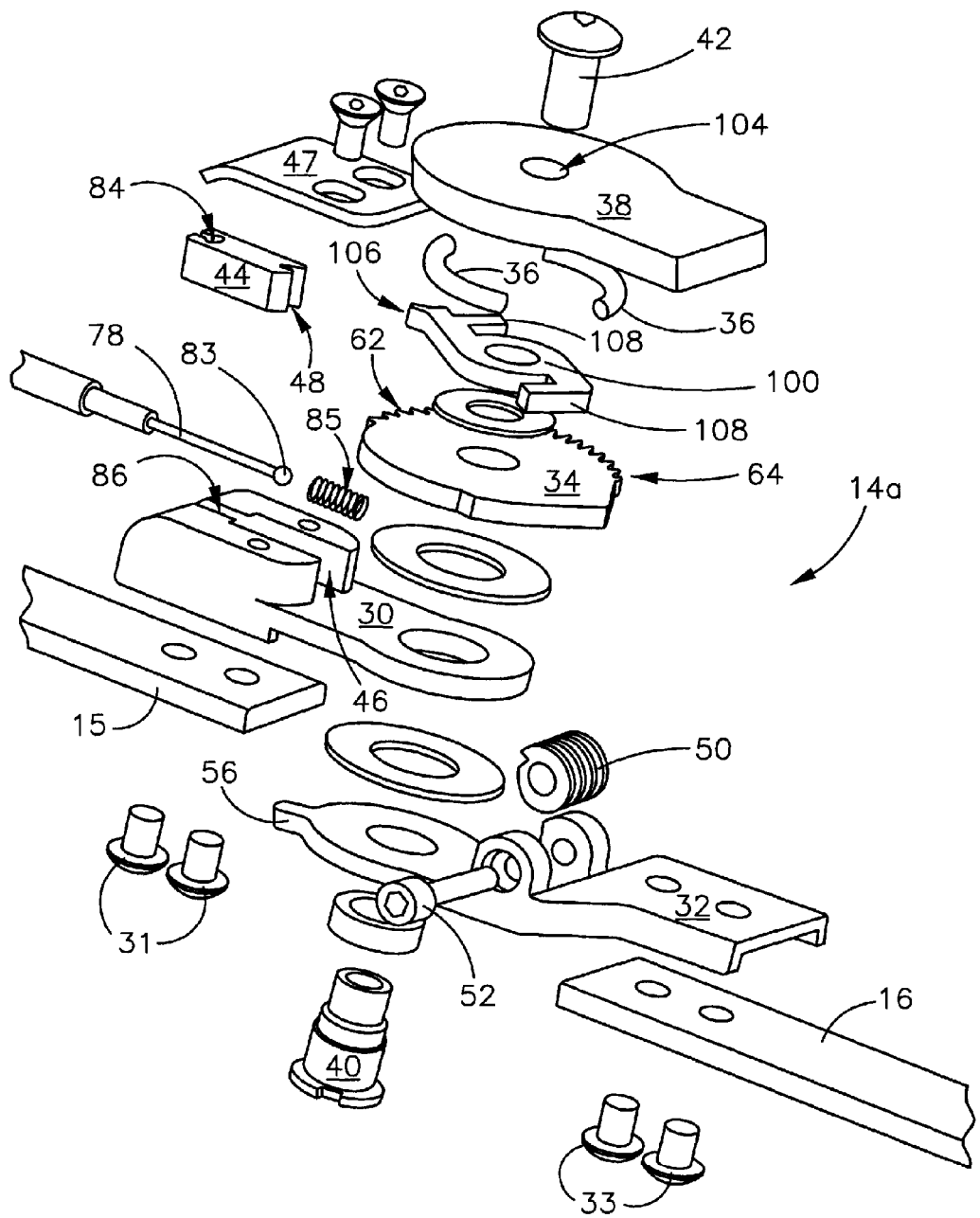
FIG. 7a illustrates an overhead, or front-side, perspective, exploded view of a lateral, left-hand alternative hinge assembly in accordance with another embodiment of the present invention.
Figure 7B:
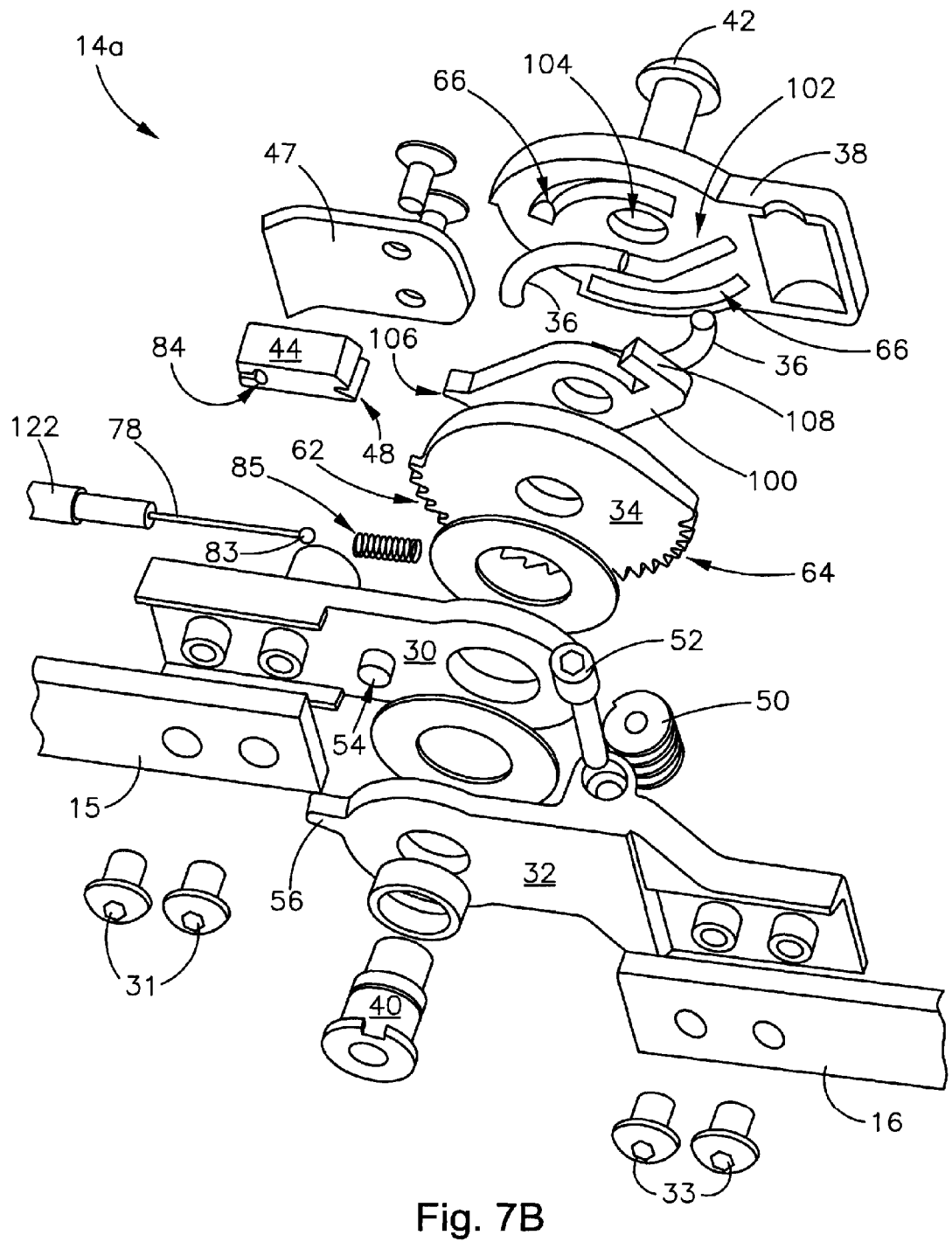

FIGS. 7a and 7b illustrate a hinge assembly 14a embodiment alternative that shown in FIGS. 3a and 3b. This latter hinge assembly 14a includes many of the same components and functionality of the hinge assembly 14 of FIGS. 3a and 3b, but does differ in at least a modified spring housing 38 and one additional component, a rotor 100, described as follows.

The spring housing 38 includes two convex, and cylindrically shaped, channels 66, each channel 66 housing an elastomeric spring 36. In this embodiment, each elastomeric spring 36 is a cylinder of urethane. Adjacent to each of the channels 66, within the spring housing 38, is a recess 102 centered about a hole 104 (through which the pivot post 40 extends) that houses the rotor 100. Within the recess 102, the rotor 100 rotates about the pivot post 40. The rotor 100 includes one or more end teeth 106, and two claws 108. The one or more end teeth 106, each geometrically complement, and are selectably engagable with, the one or more slide teeth 48. When the one or more end teeth 106 are engaged with the one or more slide teeth 48 (which occurs at full extension), rotation of the lower member 16 relative to the upper member 15 toward a flexion position causes each claw 108 of the rotor 100 to bear against a respective elastomeric spring 36 and to compress the spring 36 against its respective and confining channel 66. The elastomeric spring 36, during compression, provides resistance to the flexion of the hinge assembly 14a, and the shock absorption feature upon heel strike and weight transfer during walking. Consequently, removal of weight from a respective flexed limb results in a decompressive force of the elastomeric springs 36 upon the claws 108 of the rotor 100, which thereby urges, or assists, knee movement during the swing phase of gait from a flexion to an extension position.

Regarding the force deflection curve provided by the elastomeric springs 36, the hinge assembly 14a of FIGS. 7a and 7b functionally differs from the hinge assembly 14 of FIGS. 3a and 3b. Adjusting the range of motion (ROM) of hinge assembly 14a, through rotation of the ROM disk 34 via operation of the worm gear 50, does not effect the rotor 100 or spring housing 38 (i.e., the rotor 100 and spring housing 38 remain stationary (unaffected) by ROM adjustment). Accordingly, the claws 108 of the rotor 100 are positioned similarly, relative to a respective elastomeric spring 36, just prior to heel strike, regardless of the ROM setting.

Contrast the hinge assembly 14 of FIGS. 3a and 3b, where the spring posts 72, connected to the ROM disk 34, rotate along with the ROM disk 34 during a change to ROM setting. Accordingly, the elastomeric spring 36 may begin (i.e., just prior to heel strike) at rest (i.e., uncompressed), or may begin at various degrees of compression based upon a selected ROM setting (see FIG. 5a, where the spring 36 begins compressed with a 0° ROM setting, versus FIG. 5c, where the spring 36 begins essentially at rest with a 30° ROM setting). This difference in functionality adds to the various spring permutations, discussed above, further enabling achievement of myriad force deflection and hysteresis curves.

Figure 8:
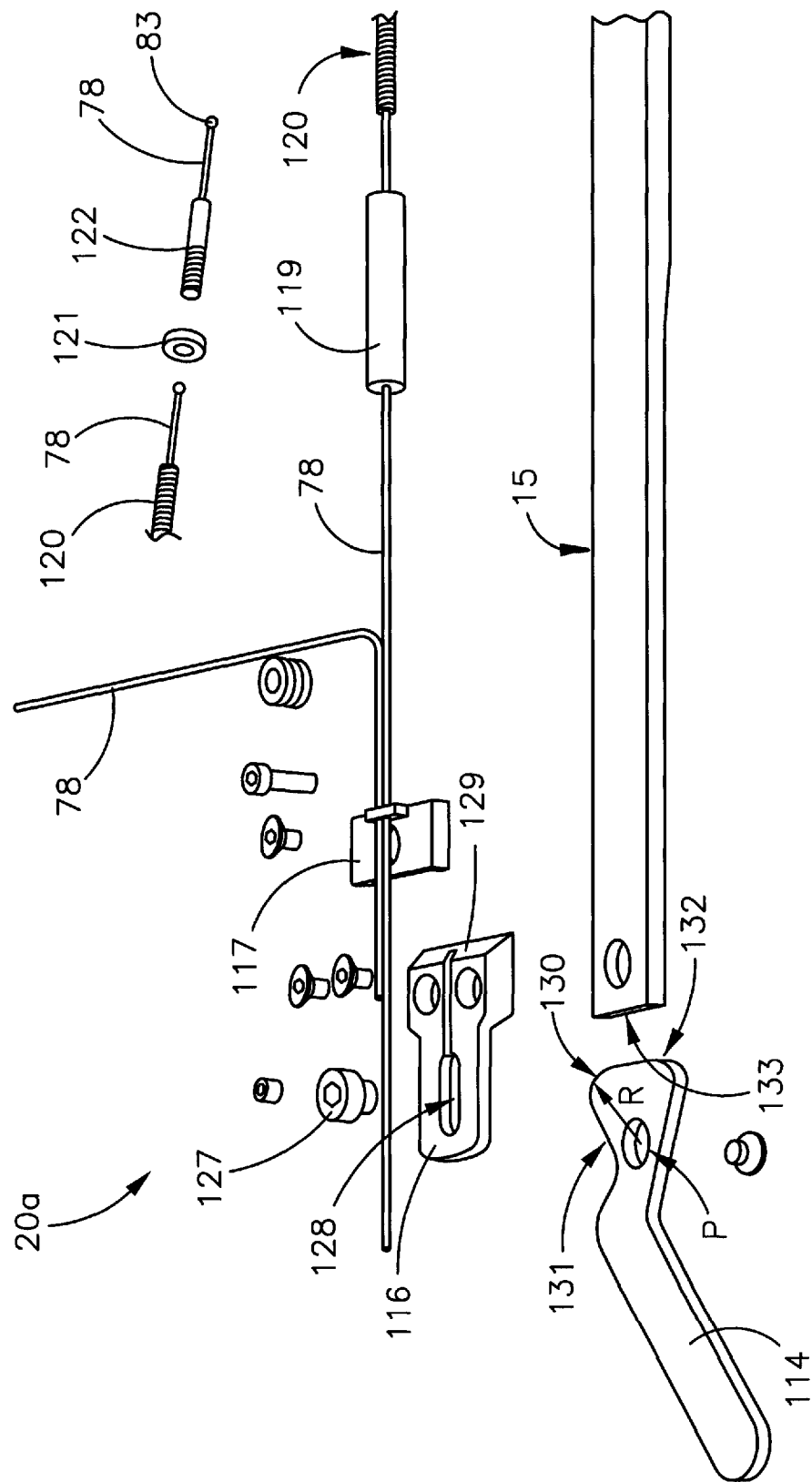
FIG. 8 illustrates a front-side, perspective, exploded view of an alternative cable release mechanism in accordance with another embodiment of the present invention.

FIG. 8 illustrates a cable release mechanism 20a embodiment alternative that shown in FIGS. 4a and 4b. This latter cable release mechanism 20a includes many of the same components and functionality of the cable release mechanism 20 of FIGS. 4a and 4b, particularly the linearity of cable 78 movement and the camming action, linearly translating the cables 78 a distance greater than that necessary to disengage the lock slide 44, without over-tensioning the respective cable 78, to provide a positive sensory and auditory feedback (snap) upon engagement, thereby ensuring the user that the cam-lock feature is fully actuated in either the engaged (locked) or disengaged (unlocked) position. This latter cable release mechanism 20a provides the similar functionality through differing components, or different forms of similar components, described as follows. Further, components are introduced for assisting the prevention of cable over-tensioning. The components, described herein, are equally adaptable for employment with the cable release mechanism 20 of FIGS. 4a and 4b.

The cable release mechanism 20a of FIG. 8 includes a lever 114, a cable lever housing 116, a cable guide 117, the two cables 78, a proximal terminal 119, a proximal compression spring 120, a locknut 121, a distal terminal 122, the distal biasing spring 85, and the bulbous cable fitting 83.

At a proximal end of the upper member 15, the cable lever housing 116 is fixedly attached to the upper member 15 with setscrews. The lever 114 is rotatably and translatably attached to the cable lever housing 116 by a binder post 127 through a slot 128 in the cable lever housing 116, the binder post 127 also securing a proximal end of the cables 78, the cables 78 lying and linearly translating within groove 129 of the cable lever housing 116.

The lever 114, like the toggle cam 76, is designed with a projecting cammed surface 130, a first flat surface 131, and a second flat surface 132, the cammed surface 130 bearing against a proximal end 133 of the upper member 15 when the lever 114 is pivoted about the binder post 127 within the slot 128. The projecting cammed surface 130, bearing against the proximal end 133 of the upper member 15, causes the binder post 127 to translate linearly within the slot 128 a sufficient distance so that the cables 78 retract the respective lock slides 44, disengaging the lock slides 44 from the spring housing 38 or the ROM disk 34 of the medial and the lateral hinge assemblies 14, 14a. The projecting cammed surface 130 incorporates a radius R (relative to the lever pivot point P) greater than a distance from pivot point P to either the first or the second flat surfaces 131, 132, which causes a toggle action and snap, under cable tension, when moving from a cammed surface 130 engagement with the proximal end 133 to either a first or a second flat surface 131, 132 engagement with the proximal end 133, thereby providing a user with a positive and certain positioning (engagement or disengagement) of the lock slide assembly 18 for each of the lateral and medial hinge assemblies 14, 14a.

Accordingly, each cable 78, when positioned in retraction, independently exerts a force greater than that of the corresponding distal biasing spring 85 to assure a force necessary to fully disengage the lock slide 44. The proximal terminal 119, the proximal compression spring 120, the locknut 121, and the distal terminal 122, enable independent adjustment of cable length and cable tensioning, thereby allowing an independent fine-tuning of each of the respective cable release mechanisms 20a.

The lever 114, due to the cammed surface 130, linearly translates the cables a distance greater than that necessary to disengage the lock slide 44 from each hinge assembly 14, 14a, and does so without over-tensioning the respective cable 78. Over-tensioning is prevented due to an over-travel allowed by a greater deflection of the proximal compression spring 120. The proximal compression spring 120 also serves to tension each cable 78 to hold (bias) one of the first or the second flat surfaces 131, 132 against the proximal end 133 of the upper member 15, thereby providing the user a positive sensory and auditory feedback (snap) upon engagement, and ensuring that the cam-lock feature is fully actuated in either the engaged (locked) or disengaged (unlocked) position.

When the lever 114 is "raked" back (as shown in FIG. 8), the second flat surface 132 (with distance from the pivot point P greater than that of the first flat surface 131) is adapted to hold the cable in a "proximally pulled" position to hold the lock slide 44 in a fully disengaged position relative to the ROM disk 34 and the spring housing 38. The proximal compression spring 120 can be adjusted to avoid an over-tensioning of the cable 78 due to the excess travel. When the lever 114 is "knuckled" forward, relative to the patient, the first flat surface 131 (with distance from the pivot point P less than that of the second flat surface 132) is adapted to enable a more distal positioning of the tensioned cable 78, first decompressing the proximal compression spring 120, then permitting the lock slide 44 to remain in a fully engaged position relative to the ROM disk 34 or the spring housing 38.

Figure 9A:
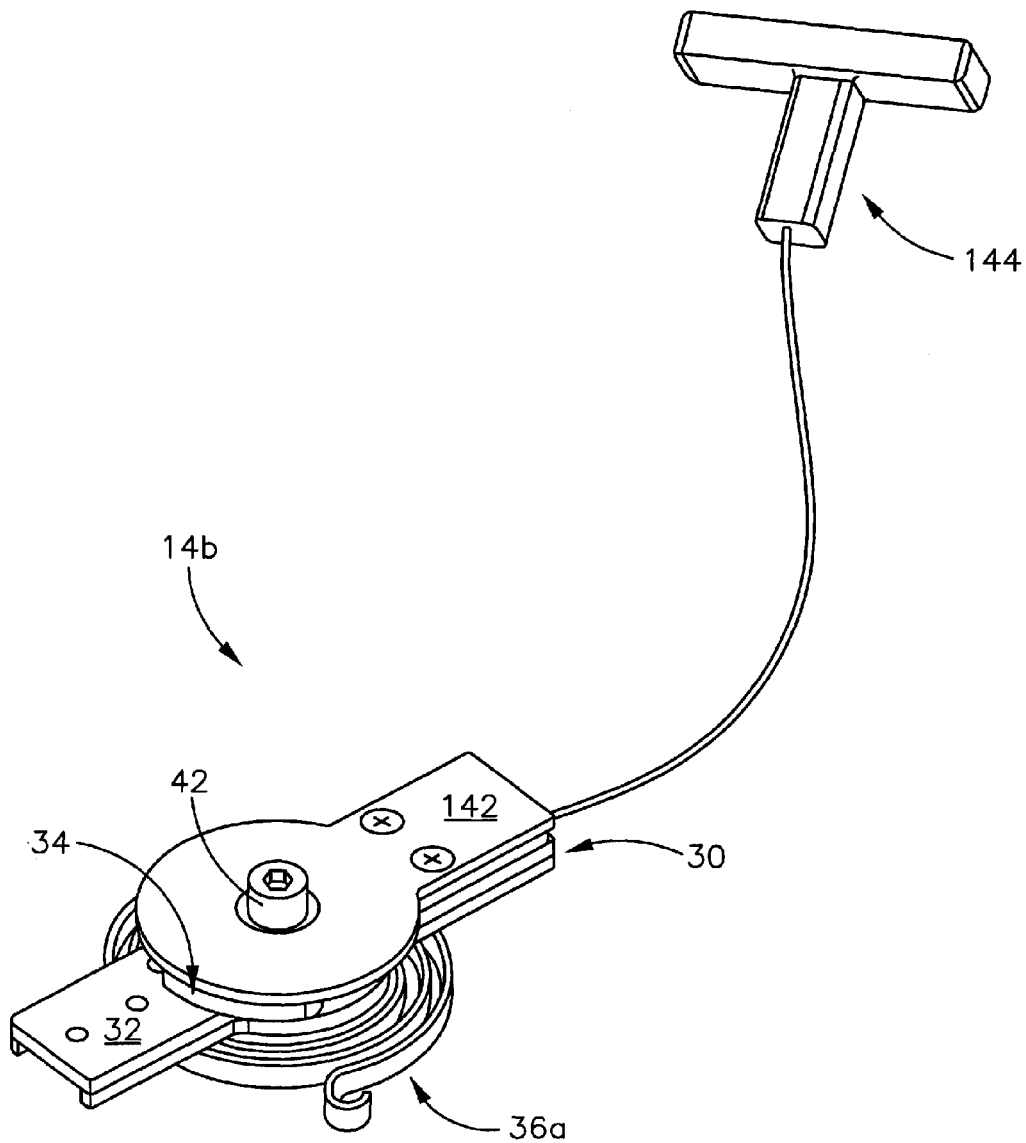
FIG. 9a illustrates an overhead, or front-side, perspective view of a hinge assembly employing a torsion spring in accordance with another embodiment of the present invention.
Figure 9B:
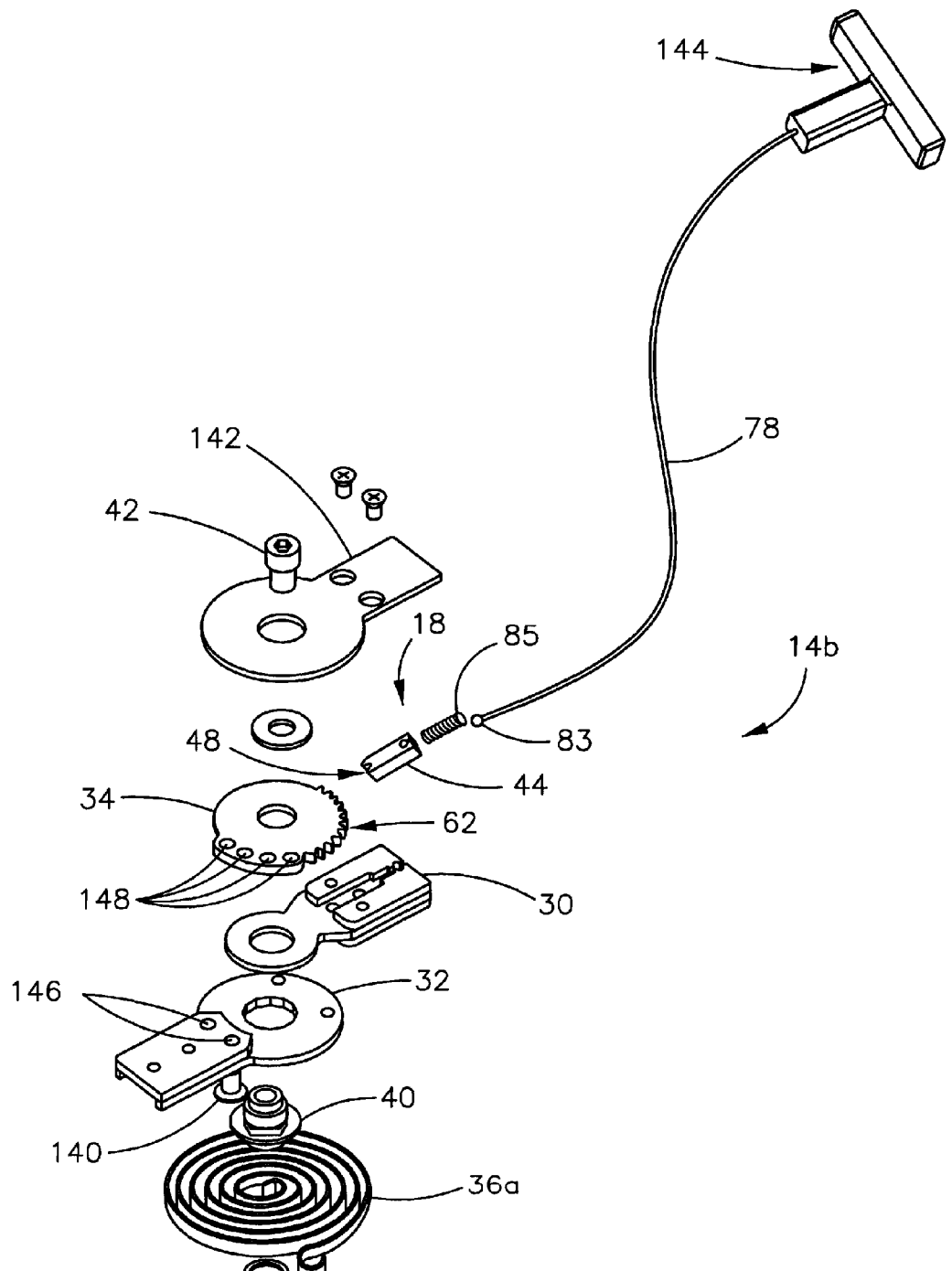

FIGS. 9a and 9b illustrate a hinge assembly 14b embodiment alternative to that shown in FIGS. 3a, 3b, 7a, and 7b. This latter hinge assembly 14b includes many of the same components and functionality of hinge assemblies 14 and 14a, of FIGS. 3a and 3b, and FIGS. 7a and 7b, respectively, but does differ in at least a modified ROM disk 34 and a torsional spring 36a, described as follows.

Referring to FIG. 9b, the hinge assembly 14b includes the torsion spring 36a, the pivot post 40, a stop pin 140, the distal half joint 32, the proximal half joint 30, the ROM disk 34, a hinge assembly cover 142, the break pin 42, and a handle 144. In this embodiment, the ROM disk 34, when is concentrically aligned with and placed on top of the proximal and distal half joints 30, 32, a top face of the ROM disk 34 lies in a same plane as a top of a raised portion of the proximal half joint 30. The ROM disk 34 is rotatably secured (free to rotate) about a circular portion of the pivot post 40 when the hinge assembly cover 142 is fixedly attached to the raised portion of the proximal half joint 30. The ROM disk includes spur teeth 62 designed to engage slide teeth 48 of the lock slide 44 (as similarly described above for the previous hinge assembly 14, 14a embodiments).

The lock slide 44, the distal biasing spring 85, the cable fitting 83 and the cable 78 (lock slide assembly 18 components) are housed within and cooperate with the proximal half joint 30 as described above for the previous hinge assembly 14, 14a embodiments. In this embodiment, however, a simple handle 144 is used to manipulate the lock slide assembly 18, rather than the cable release mechanisms 20, 20a previously presented.

The stop pin 140 is placed through one of a plurality (two in this embodiment) of stop pin holes 146 in the distal half joint 32, and threaded into one of a plurality (four in this embodiment) of stop pin holes 148 in the ROM disk 34, resulting in the ROM disk 34 and the distal half joint 32 rotating as one about the pivot post 40. Placement of the stop pin 140, as described, provides an adjustable flexion stop (i.e., maximum degree of flexion), preventing a knee (in the case of employment in a knee brace) from buckling past a certain angle. The embodiment of FIGS. 9a and 9b can be adjusted to the following ranges: 0-20°, 0-40°, or 0-60°.

As previously described, the lock slide assembly 18 cooperates with the ROM disk 34 (i.e., biased slide teeth 48 engagement with the spur teeth 62) to provide a one-way, step advance (ratcheting) from pre-determined positions of flexion to pre-determined positions of extension (i.e., allowing the hinge assembly 14b to rotate toward full extension (180°), but not allowing intermittent rotation toward flexion). If the user desires flexion beyond the pre-set range of motion (e.g., to full flexion for acquiring a sitting position), the slide teeth 48 are disengaged from the spur teeth 62 by pulling the handle 144, which compresses the spring 85 to remove the biasing force of the lock slide 44.

A hex-shaped portion of the pivot post 40 is placed within a 12-sided hole in the distal half joint 32 (an arrangement identical to a 12-point socket and a hex head screw). A bottom of the pivot post 40 is slotted to accept a tang of the torsion spring 36a. Torsion spring 36a tension is augmented by re-indexing (turning) the hex of the pivot post 40 within the dodecagon. A loop, or hook, at an opposite end of the torsion spring 36a communicates with a protruding tab on the proximal half joint 30 or on the upper member 15. Increasing tension increases dampening of shock absorption during heel strike, and further assists a lower limb during the swing phase of gait. This configuration is also suitable for managing joint stiffness and contracture as adjustable tensioning of soft tissues with a torsion spring is very effective.

Bi-directional Hinge Assembly Embodiments

FIGS. 10-17 illustrate bi-directional embodiments of the hinge assembly directed to the ankle and knee. The bi-directional embodiments can be incorporated into orthotic, prosthetic, or rehabilitative devices where elastomer restraints are provided with set screws in channels to control flexion and extension (clockwise and counterclockwise) moments.

An ankle embodiment is illustrated in FIGS. 10-15 that controls dorsi and plantar flexion moments generated by ground reaction forces in a patient, and particularly in a stroke patient. The ankle embodiments include elastomer restraints configured so that, while one elastomer spring compresses, another decompresses at the same time, providing a dynamic fine-tuning to the adjustable shock absorption at initial heel contact and through gait with return hysteresis. Alternatively, the ankle embodiments could include elastomer restraints configured so that, while one elastomer spring compresses, the other remains idle, and only acts upon opposite direction movement established in another dampening range of motion (ROM).

A knee embodiment is illustrated in FIGS. 16-17 that provides dual elastomer restraints to allow bi-directional dampening of angular movement in each of a clockwise and counterclockwise direction from a user selected position. The knee embodiment also provides assistance in angular movement back to the user selected position from and after the resisted angular movement from the user selected position.

The principles and concepts of the present invention can be used in hinge and joint assemblies generally, can be used in an orthotic and/or rehabilitative embodiment as taught and described herein, or can be used in a prosthetic embodiment as modified by those with skill in the art from an appreciation of the present invention. Further, in addition to use in joint and hinge assemblies generally, the present invention can be specifically directed to devices supporting any flexible ligamentous joint, such as the wrist, elbow, shoulder or hip, and can be adapted to mimic, assist, and/or support any muscle or tissue, including providing adjustable corrective or therapeutic force for the reduction of joint and muscle stiffness, contracture, or for management of spasticity.

In one aspect of the bi-directional embodiments, a hinge assembly includes a first member movably connected to a second member to allow angular displacement of the first member relative to the second member in each of extension and flexion (clockwise and counterclockwise) directions, where one elastomeric spring communicating with the first and the second members restrains angular displacement in a flexion position, and another elastomeric spring communicating with the first and the second members restrains angular displacement in an extension position. In each direction, the angular movement is dampened through compression of the respective elastomeric spring. After dampening the movement in either direction, returning angular movement is assisted through decompression of the respective elastomeric spring. The elastomeric spring can be adapted to provide a pre-determined force deflection curve in compression and an independent rate of return hysteresis in decompression. The elastomeric springs could be urethane.

In another aspect, the elastomer restraints are provided with set screws in channels to control dorsi and plantar flexion moments. Each set screw adjusts a size of the a respective channel, thereby applying or relieving channel compressing forces on the respective elastomer spring, which thereby adjust the dampening shock absorption forces provided by the elastomer during further compression, and subsequent assistance forces provided by the elastomer during decompression.

In another aspect, the elastomer restraints are configured so that, while one elastomeric spring compresses, another decompresses at the same time, providing a dynamic fine-tuning to the dampening and assistance forces; for example, providing adjustable shock absorption at initial heel contact and through gait with return hysteresis.

Other embodiments provide a hinge assembly including a proximal member movably connected to a distal member to allow angular displacement of the proximal member relative to the distal member, two spring housings communicating with the proximal and the distal members, where movement of the spring housings track, and are tracked by, movement of one of the proximal or the distal members. In this aspect, the hinge assembly further includes a first elastomeric spring in bearing engagement with a respective first spring housing, and a second elastomeric spring in bearing engagement with a respective second spring housing. Angular displacement of the proximal member relative to the distal member from an initial point in a first direction compresses the first elastomeric spring (or both elastomeric springs) to dampen the angular displacement in the first direction, where decompression of the first elastomeric spring (or both elastomeric springs) urges angular displacement of the proximal member relative to the distal member in a second direction back to the initial point. Further, angular displacement of the proximal member relative to the distal member from the initial point in the second direction compresses the second elastomeric spring (or both elastomeric springs) to dampen the angular displacement in the second direction, where decompression of the second elastomeric spring (or both elastomeric springs) urges angular displacement of the proximal member relative to the distal member in the first direction back to the initial point. The spring housing can include a channel to keep each elastomeric spring, each elastomeric spring then compressing against inner walls of the channel.

In these embodiments, the hinge assembly could further include a worm gear, and a disk or wheel with a plurality of worm teeth, the worm gear and the worm teeth being engagably positioned so that operation of the worm gear engages the worm teeth to lock the proximal member relative to the distal member, thereby setting the bi-directional range of dampening and returning assistance action. This dampening range of motion (ROM) could be any selected range less than 360°, and the worm gear and associated wheel with worm teeth could be configured for engagement capability over the 360° range.

Bi-directional Ankle Embodiment

Figure 10A:
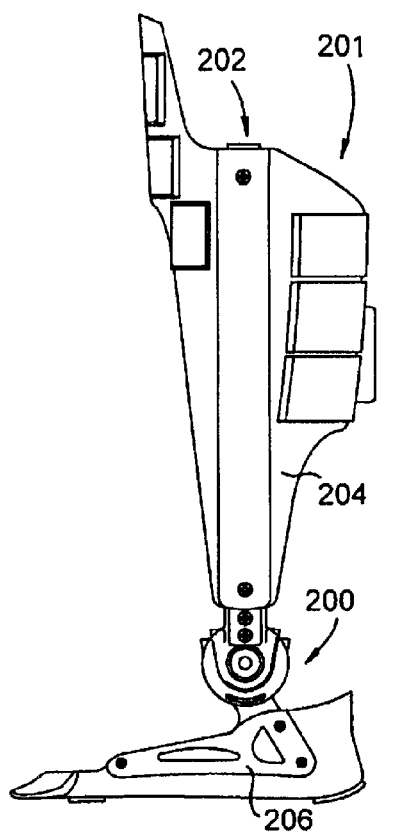
FIGS. 10a and 10b illustrate an orthotic ankle brace in accordance with another embodiment of the present invention.
Figure 10B:
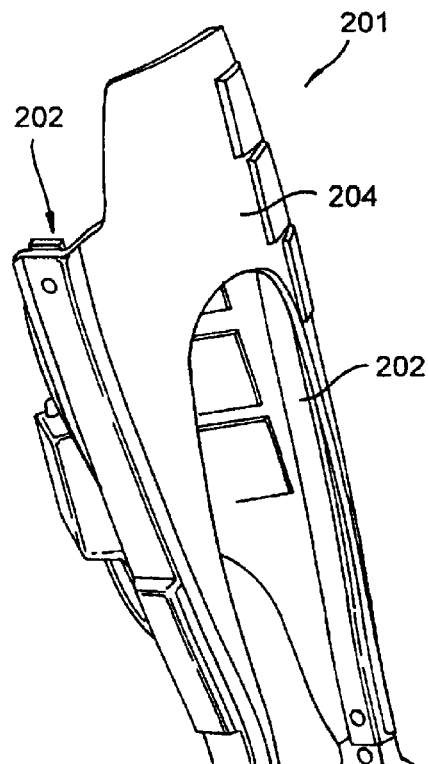

FIGS. 10a and 10b illustrate a bi-directional ankle embodiment, or ankle joint 200, of the present invention. The bi-directional ankle joint 200 is shown mounted onto a ground reaction AFO, or leg and foot brace 201. The leg and foot brace 201 includes leg beams 202 mounted under a plastic shell 204 of the brace 201 to insure intimate fit and low profile. Two bi-directional ankle joints 200 are included in the brace 201, and each include a low profile-high support contoured strut 206 (proximal and distal), thereby allowing in-shoe wear of the brace 201 without requiring increased size shoe.

Figure 11A:
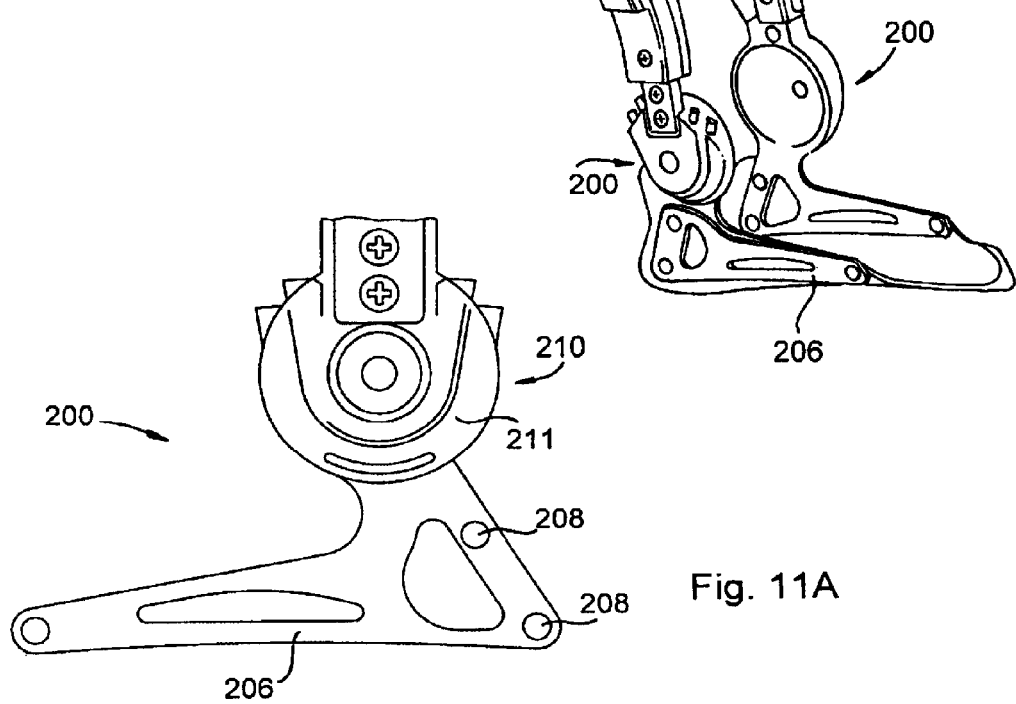
FIG. 11a illustrates an outer view, and FIG. 11b an inner view, of a bi-directional ankle joint (hinge) assembly within the ankle brace of FIGS. 10a and 10b.
Figure 11B:
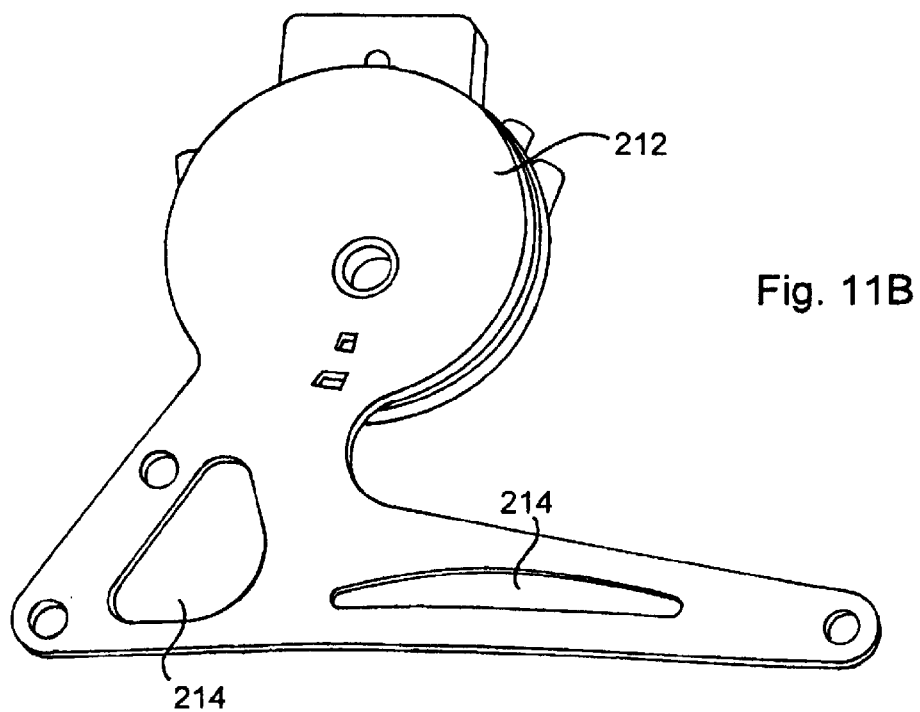

FIGS. 11a and 11b illustrate the bi-directional ankle joint 200 alone. The strut 206 is low profile and slim, with three mounting holes 208 that follow foot anatomy and hug the respective surface of the foot. The ankle hinge 210 has a cupola design, and includes an outer 211 and inner 212 surface that fits perfectly over the bony prominence of the ankle, while providing uncommon strength to the joint 200. The inner surface 212 of the ankle hinge 210 is fixedly connected to, or is one with, the strut 206. Cutouts 214 within the strut 206 ensures even load transfer from ankle joint 200 to strut 206, while minimizing weight of the joint 200 due to an material omission in low stress areas.

Figure 12A:
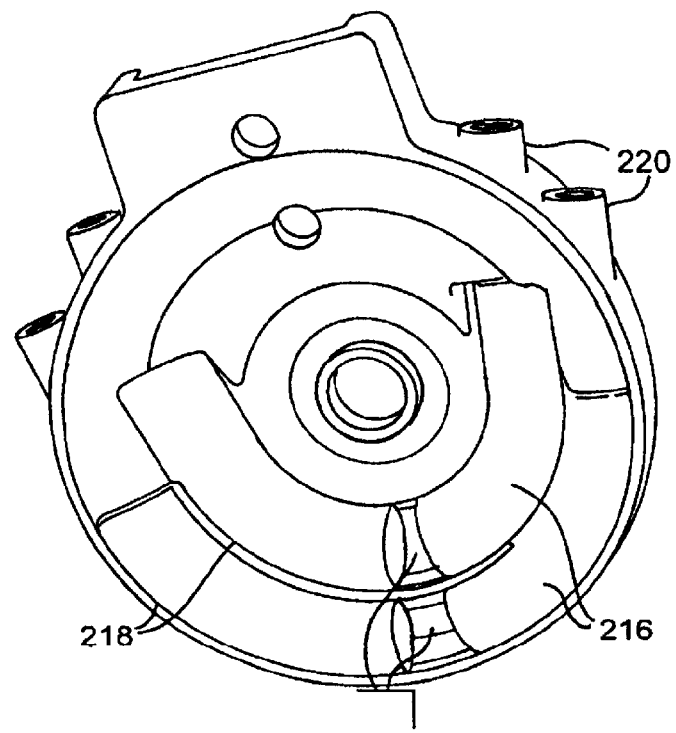
FIG. 12a illustrates the ankle joint assembly of FIGS. 11a and 11b with the inner cover removed.

FIG. 12a illustrates the ankle hinge 210 with inner surface 212 and strut 206 removed to show elastomer springs 216, spring channels 218 and adjustment screws 220. The elastomer springs 216 fit within respective spring channels 218 to provide desired shock absorption during heel strike and terminal stance, and desired assist during respective plantarflexion or dorsiflexion. The adjustment screws 220 regulate an amount of breaking and assistance forces by adjusting a relative fit of a respective elastomer spring 216 within its spring channel 218.

Figure 12B:
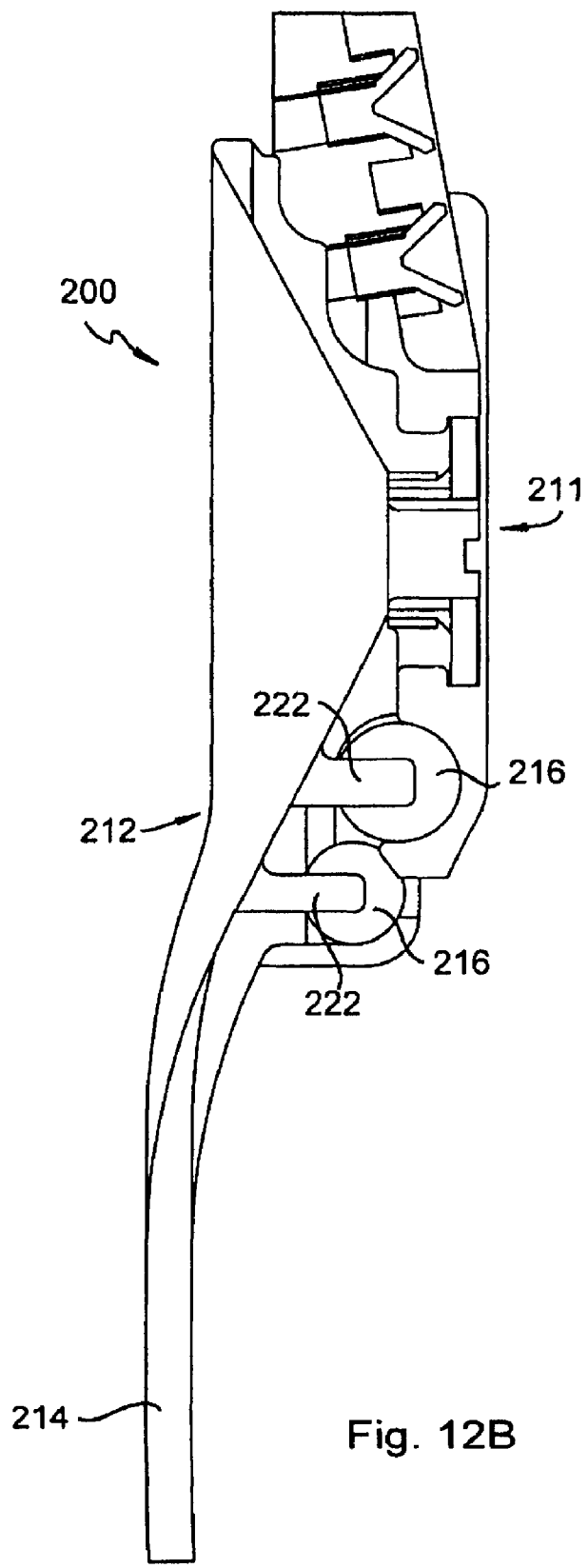
FIG. 12b illustrates a cross-sectional view of the ankle joint assembly of FIGS. 11a and 11b.

FIG. 12b illustrates a vertical cross-section of the ankle joint 200, showing protrusions 222 that are fixed to the inner surface 212 of the ankle hinge 210 and the strut 206. The protrusions 222 extend into each of the spring channels 218 between the respectively and serially aligned elastomer springs 216. In FIG. 12a, protrusions 222 (not shown) are located within the spring channels 218 at reveal 223. The protrusions 222 act to load the elastomer springs 216 during gait sequence.

Tertiary control over dynamic response of the elastomer springs 216 can be accomplished by: 1) varying material characteristics of the elastomer polymer involved; and 2) varying an amount of space (i.e., size of elastomer spring 216 and/or size of spring channel 218) that the elastomer spring 216 can expand into during compression. These varying characteristics provide a intricate degree of control over breaking forces and their responding transient hysteresis. In the bi-directional ankle embodiments illustrated herein, where four (4) elastomeric springs 216 are implemented, one or more of the elastomer springs 216 could separately be a multi-segmented element, or could separately be of varying material, length, girth, etc., to further tailor dynamic response to patient need. In addition, any number of elastomeric springs 216 could be implemented, depending on contribution to dynamic response and satisfaction of patient need.

Figure 13:
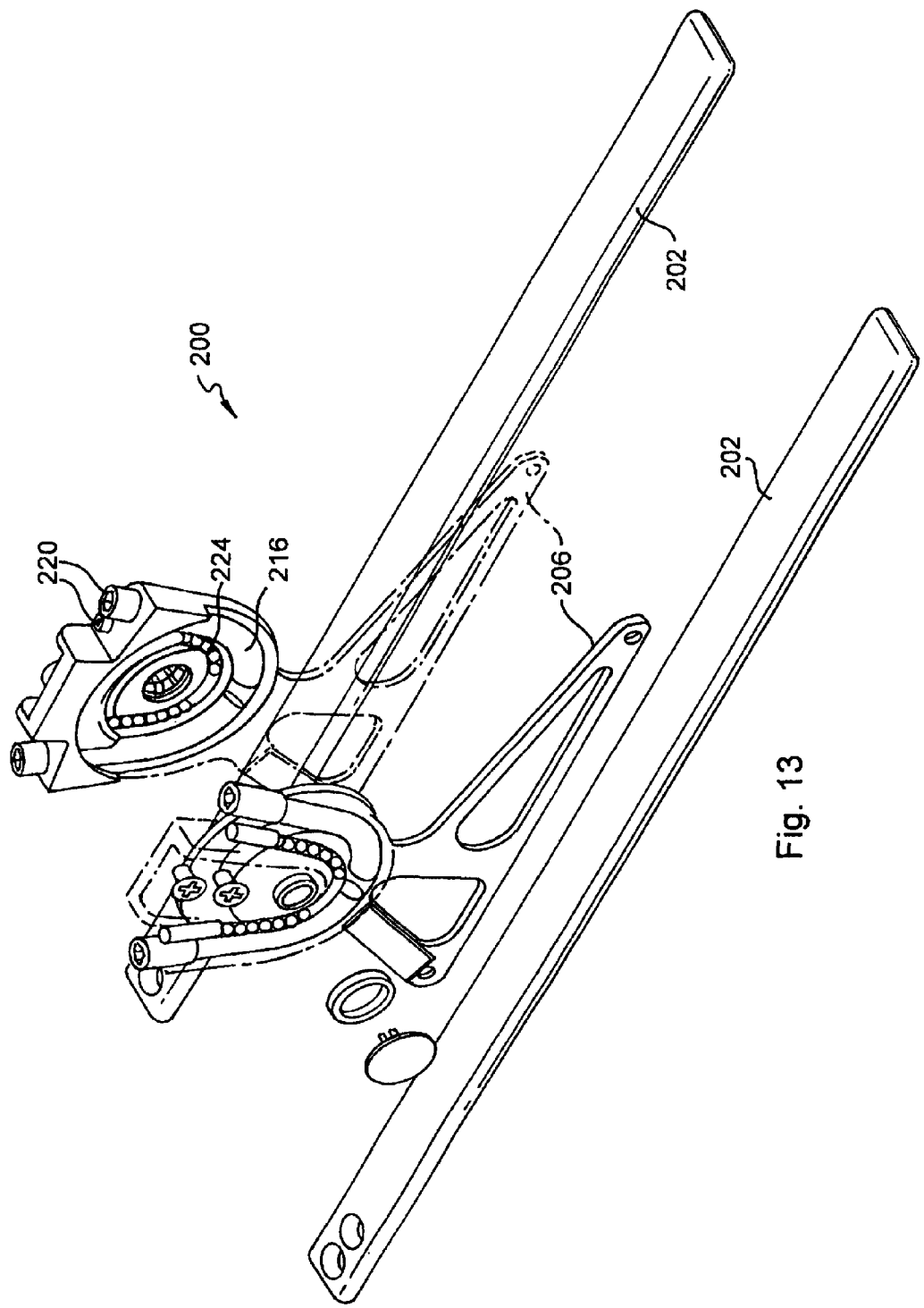
FIG. 13 illustrates an alternative embodiment of the ankle joint assembly of FIGS. 11a and 11b, FIG. 13 having providing a transparent view to show inner components.

FIG. 13 illustrates an alternative embodiment of the bi-directional ankle joint 200, where the ankle hinge 210 includes cylindrical elastomer springs 216 (as previously shown) in an outer spring channel 218, and ball bearings 224 in an inner spring channel 218. In this embodiment, the ball bearings 224 provide hard limits to the range over which the elastomer springs 216 can provide dampening and assistance forces, as shown in FIG. 14.

Figure 14:
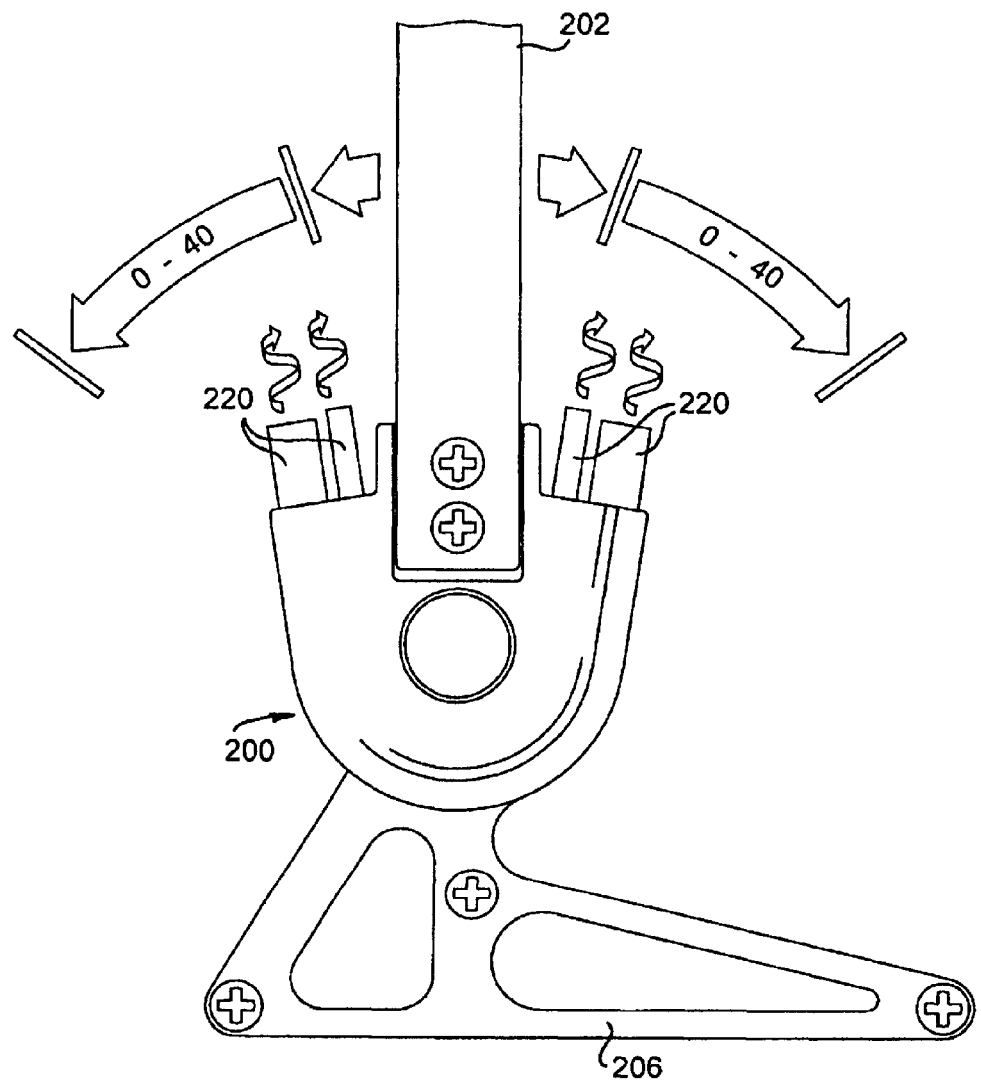
FIG. 14 illustrates an adjustable operating range of motion, and accompanying dampening range of motion, provided by the ankle joint assembly of FIGS. 11a and 11b.
Figure 15:
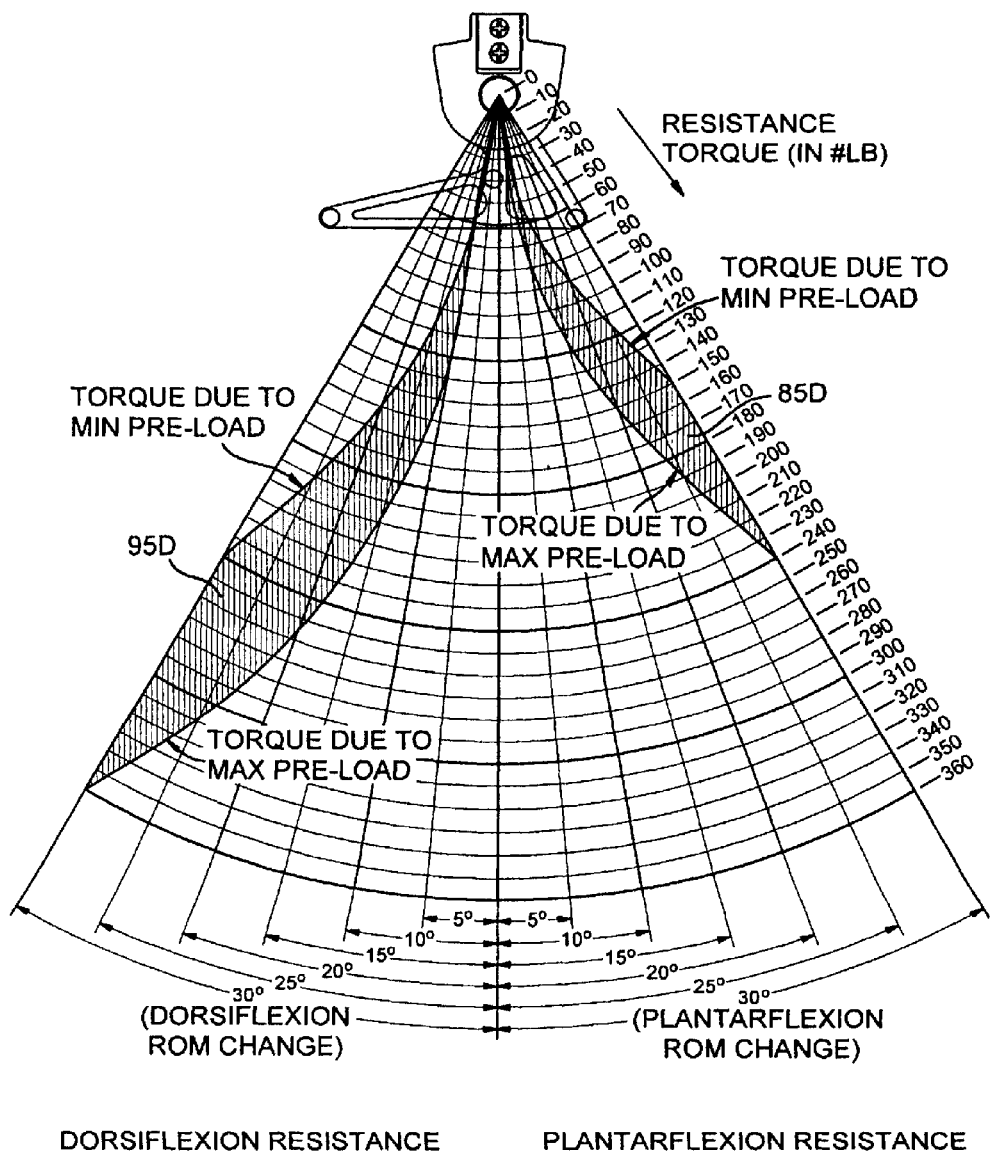
FIG. 15 illustrates torque resistance curves provided in dorsiflexion and plantarflexion motion by the ankle joint assembly of FIGS. 11a and 11b.

FIG. 14 illustrates a movable range over which the elastomer springs 216 provide dampening and assistance forces, as defined by inner adjustment screws 220. Inner adjustment screws (as shown in FIG. 14) 220 define a 0°-40° plantarflexion and a 0°-40° dorsiflexion range of motion (ROM). Outer adjustment screws 220 tailor the dynamic dampening and assistance response. In one embodiment, adjustable dampening muscle compensation of up to 240 in-lb in plantarflexion, and up to 360 in-lb in dorsiflexion, can be provided. FIG. 15 illustrates torque generated dependence on plantarflexion/dorsiflexion range of motion in the illustrated ankle embodiment.

Accordingly, the ankle joint 200 illustrated in FIGS. 10-11 is generic to the four (4) elastomer spring 216 embodiment of FIG. 12 and the two (2) elastomer spring 216 and ball bearing 224 embodiment of FIG. 13. In either of the FIG. 12 or 13 embodiments, the protrusions 222 (one in each semi-circular spring channel 218) act to compress a respective one of each elastomer spring 216 pair, while allowing the other of the elastomer spring 216 pair either remain idle, or to decompress, during either a flexion or extension movement of the joint, depending on a loading imposed thereon by a respective adjustment screw 220. Note that the protrusions 222 could just as effectively communicate with the outer surface 211 of the ankle hinge 210 (with translation to the leg beams 202), rather than communicate with the inner surface 212 of the ankle hinge 210 and strut 206, as illustrated.

As detailed above, adjustment screws 220, located at each end of each semi-circular spring channel 218, act to regulate the amount of assist and breaking force associated with each elastomer spring 216, by allowing a user to load each elastomer spring 216 individually against its respective protrusion 222, and against its respective spring channel 218 wall. Accordingly, this loading of any/each elastomer spring 216 while the ankle joint 200 is at rest provides that, during any angular joint displacement, one elastomer spring 216 can be compressing to provide shock absorption while the other of the pair decompresses at the same time. This feature provides a dynamic fine-tuning to the dampening and assistance forces of the ankle joint 200 of the present invention.

In the FIG. 13 (two (2) elastomer spring 216 and ball bearing 224) embodiment, the respective protrusion 222 interacting with the ball bearings 224 provides maximum limits to the range of motion of the joint. Depending on the number and size of the ball bearings 224 in the respective spring channel 218, as well as the position of respective adjustment screws 220, maximum limits to the range of motion (ROM) are defined. Accordingly, the maximum range of motion can be individually selected for each of dorsiflexion and plantarflexion moments.

Bi-directional Knee Embodiment (Adaptable to Any Flexible Ligamentous Joint)

Figure 16A:
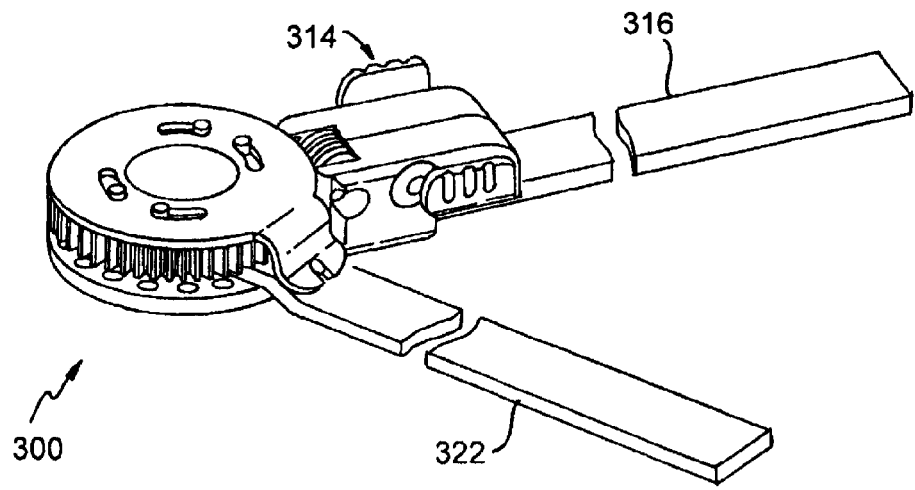
FIG. 16a illustrates a bi-directional knee joint (hinge) assembly, and FIG. 16b an accompanying companion joint assembly, in accordance with another embodiment of the present invention.
Figure 16B:
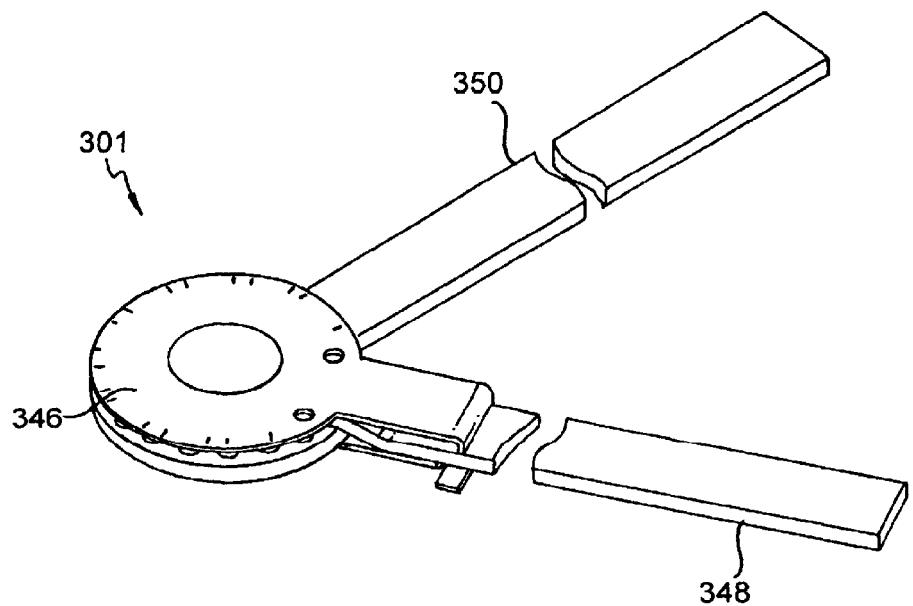
FIG. 16c illustrates an exploded view of the bi-directional knee joint and accompanying companion joint of FIGS. 16a and 16b, respectively.
Figure 16C:
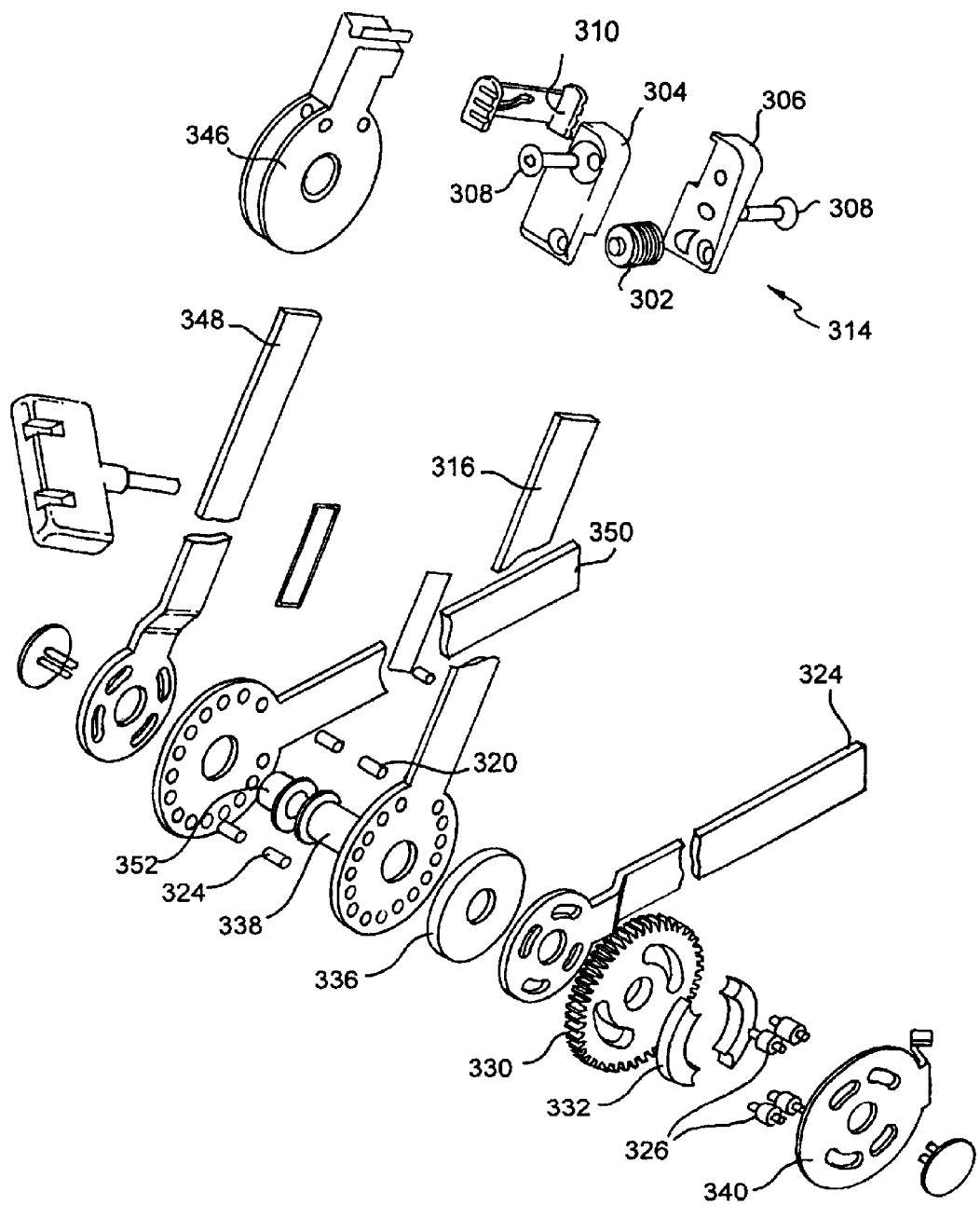

FIGS. 16*a*, 16*b* and 16*c* illustrate a bi-directional knee embodiment of the present invention. FIG. 16*a* illustrates a bi-directional knee joint 300, and FIG. 16*b* illustrates its accompanying companion joint 301. The bi-directional knee joint 300 and accompanying companion joint 301 are each worn within a knee brace, one on each side the knee. The bi-directional knee joint 300 provides dampening resistance and assistance in two directions of rotational movement, while the companion joint 301 mimics the dampened movement of the spring-loaded knee joint 300, and provides rigid support within the brace for its respective side of the knee. FIG. 16*c* illustrates an exploded view of each of the bi-directional knee joint 300 of FIG. 16*a* and the accompanying companion joint 301 of FIG. 16*b*.

The bi-directional knee joint 300 provides controlled, multi-position rotational motion to each of extension and flexion (clockwise or counterclockwise) directions, from a user selected angular starting point, to prevent knee buckling or knee hyperextension, and/or to rehabilitate a particular angular range of movement from myriad pre-selected angular starting points. Resistance to both extension and flexion is provided through two elastomer springs, enabling a dampening shock absorption feature in each direction, depending on ever varying knee bending movements.

In one aspect of the invention, and that illustrated in FIG. 16*a*, the bi-directional (or double action) dampening knee joint 300 acts about a range of motion totaling 280°. A user, anywhere within this 280° range, can engage a worm gear within a sprocket wheel to activate the dampening (and returning assistance) over a 20° increment in each of a flexion and extension direction.

Figure 17A:
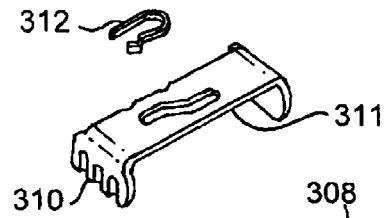
Figure 17A:
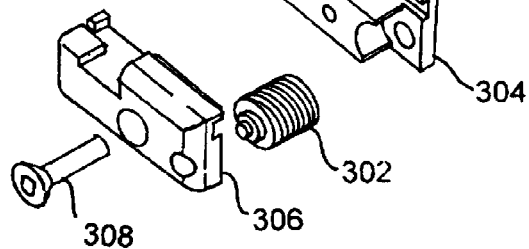
Figure 17B:
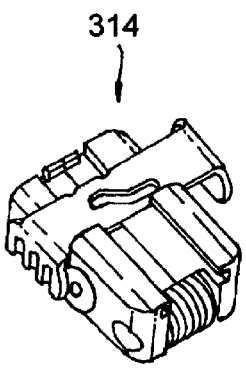

FIGS. 17*a* through 17*l* illustrate assembly of, and interaction between, the various components of the bi-directional knee joint 300 of FIG. 16*a*. In FIG. 17*a*, a worm gear 302 is placed between inner 304 and outer 306 housing components, as shown, and all are attached by screws 308. A lock plate 310 having an s-shaped slot 311 is placed over the housings 304, 306, in the orientation shown, and is preloaded with pin 312. An assembled worm housing 314 is shown in FIG. 17*b*.

Figure 17C:
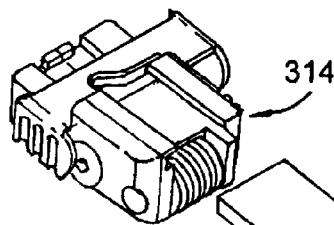
Figure 17C:
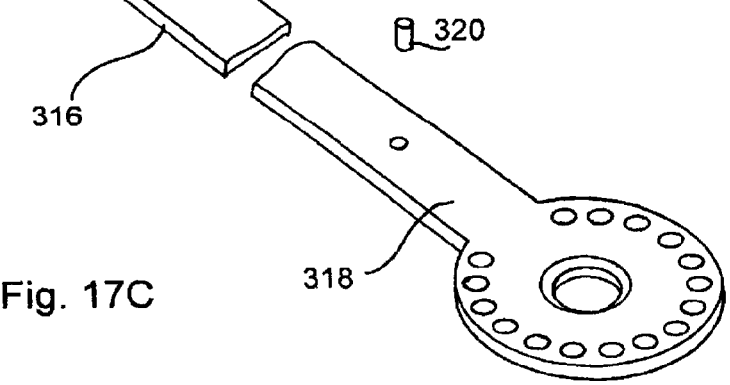

The worm housing 314 is slid along a proximal strut 316 to proximal stop 318 (FIG. 17*c*). A proximal lock-pin 320 is pressed through the proximal strut 316 and into the s-shaped slot 311 of the lock plate 310. An assembled proximal strut assembly 321 is shown in FIG. 17*d*. Operation (movement) of the lock plate 310 (perpendicular to the proximal strut 321) causes the worm housing 314 to slidably translate (approximately ¼") along the proximal strut 316 due to proximal lock-pin 320 engagement within the s-shaped slot 311 of the lock plate 310.

Separately, a distal strut 322 receives a distal lock-pin 324 (FIG. 17*e*), which is pressed therein until the lock-pin 324 bottoms out, below, and protrudes approximately 1/16" above (as shown) the distal strut 322. An assembled distal strut assembly 325 is shown in FIG. 17*f*.

Still separately, and as shown in FIG. 17*g*, a pusher pins 326 (four (4) total) are located within and at each end of two (2) spring channels 328 of a toothed wheel (disk) gear 330. Elastomer springs 332 (two (2) total) are placed between respective pusher pins 326 in each of the two (2) spring channels 328. The elastomer springs 332 may be loaded (compressed) upon placement. An assembled wheel gear assembly 334 is shown in FIG. 17*h*.

From FIG. 17*i*, the wheel gear assembly 334, distal strut assembly 325, washer(s) 336, and the proximal strut assembly 321 are arranged (stacked) as shown over rivet 338 (FIG. 17*j*). A cover plate 340 (FIG. 17*k*) is placed about the rivet 338 with pusher pins 326 protruding through crescent shaped cover slots 342 (one pusher pin 326 per cover slot 342), as shown in FIG. 17*l*. The cover plate 340 further includes an angled member 343 with groove 344. The groove 344 accepts the distal lock-pin 324 of the distal strut 322, thereby assuring that radial movement of the cover plate 340 about the rivet 338, relative to the proximal strut 316, mimics that of the distal strut 322. The rivet 338 is swaged about the cover plate 340, clamping the knee joint 300 together (FIG. 17*l*).

Referring now to FIGS. 16*b* and 16*c*, the companion joint 301 includes retaining plate 346, companion distal strut 348, companion proximal strut 350 and companion rivet 352. The companion distal strut 348 and the companion proximal strut 350 are placed coaxially, as shown, the retaining plate 346 is placed thereover, and the companion rivet 352 placed therethrough. The companion rivet 352 is swaged about the retaining plate 346, clamping the companion joint 301 together.

During operation, the lock plate 310 can be slid back and forth, perpendicular to the proximal strut 321, to slidably translate the worm housing 314 approximately ¼" back and forth along the proximal strut 316. Engagement of the fixed proximal lock-pin 320 within the s-shaped slot 311 of the lock plate 310 moves the worm gear 302 into and out of engagement with outer teeth of the wheel gear 330 upon operation of the lock plate 310. Accordingly, a range of motion of the knee joint 300 to provide bi-directional dampening and assistance is user selected by operation of the lock plate 310.

In the knee joint 300 embodiment illustrated in FIGS. 17*a*-17*l*, a 280° total range of motion is available. Within the 280° range of motion, any 40° increment (i.e., 20° in each direction) can be selected as the safety and therapeutic range (i.e., range providing bi-directional dampening and assistance). A user would first operate the lock plate 310 to disengage the worm gear 302 from the wheel gear 330, rotate the proximal strut 316 relative to the distal strut 322 to a desired position, then operate the lock plate 310 to engage the worm gear 302 with the wheel gear 330. Dampening and assistance is now provided within a 20° range on either side of the desired location. The FIG. 17 embodiment can be easily modified to support any flexible ligamentous joint, such as the wrist, elbow, shoulder or hip. Only the proximal 316 and distal 322 struts would require size/shape modification to accommodate the particular joint. Therefore, hinge assemblies of the present invention can be adapted to mimic, assist, and/or support any muscle or tissue, including providing adjustable corrective or therapeutic force for the reduction of joint and muscle stiffness, contracture, or for management of spasticity.

In operation, the knee joint 300 provides that the proximal strut 316 is movably connected to the distal strut 322 to allow angular displacement of the proximal strut 316 relative to the distal strut 322. This embodiment also provides two (2) spring channels 328 communicating with the proximal 316 and the distal 322 struts, where movement of the spring channels 328 track, and are tracked by, movement of the proximal 316 and/or the distal 322 struts. Further, the knee joint 300 includes two (2) elastomer springs 332, one (1) elastomer spring 332 in bearing engagement with each spring channel 328. Angular displacement of the proximal strut 316 relative to the distal strut 322 from an initial point in a first direction compresses both elastomer springs 332 to dampen the angular displacement in the first direction, where decompression of the elastomer springs 332 urges angular displacement of the proximal strut 316 relative to the distal strut 322 in a second direction back to the initial point. Further, angular displacement of the proximal strut 316 relative to the distal strut 322 from the initial point in the second direction compresses both elastomer springs 332 to dampen the angular displacement in the second direction, where decompression of the elastomer springs 332 urges angular displacement of the proximal strut 316 relative to the distal strut 322 in the first direction back to the initial point.

These and other advantages of the present invention will be apparent to those skilled in the art from the foregoing specification. Accordingly, it is recognized by those skilled in the art that variations or modifications may be made to the above-described embodiments without departing from the broad inventive concepts of the invention. It is therefore understood that this invention is not limited to the particular embodiments described herein, but is intended to include all possible variations and modifications within the scope and spirit of the invention.

What is claimed is:

1. A hinge assembly comprising:
   a first member movably connected to a second member to allow angular displacement of the first member relative to the second member in each of a clockwise and counterclockwise direction;
   at least one elastomeric spring communicating with the first and the second members to restrain angular displacement in a clockwise direction through compression of the at least one elastomeric spring, and to assist angular displacement in a counterclockwise direction through decompression of the at least one elastomeric spring; and
   at least one other elastomeric spring communicating with the first and the second members to restrain angular displacement in a counterclockwise direction through compression of the at least one other elastomeric spring, and to assist angular displacement in a clockwise direction through decompression of the at least one other elastomeric spring.

2. The hinge assembly of claim 1, wherein the at least one other elastomeric spring decompresses when the at least one elastomeric spring compresses.

3. The hinge assembly of claim 1, wherein the at least one elastomeric spring decompresses when the at least one other elastomeric spring compresses.

4. The hinge assembly of claim 1, wherein a time rate of compression of the at least one, and the at least one other, elastomeric spring in response to a force is faster than a subsequent time rate of decompression of the at least one, and the at least one other, elastomeric spring resulting from the force.

5. The hinge assembly of claim 1, wherein the at least one, and the at least one other, elastomeric spring is selectively designed, in size, shape and density, to provide a pre-determined force deflection curve in compression and a rate of return hysteresis in decompression.

6. A hinge assembly comprising:
   a proximal member movably connected to a distal member to allow angular displacement of the proximal member relative to the distal member;
   a first and a second spring channel communicating with each of the proximal and the distal members; and
   a first elastomeric spring in bearing engagement with a first spring channel, and a second elastomeric spring in bearing engagement with the second spring channel, wherein angular displacement of the proximal member relative to the distal member from an initial point in a first direction compresses the first elastomeric spring to dampen the angular displacement in the first direction, and decompression of the first elastomeric spring urges angular displacement of the proximal member relative to the distal member in a second direction back to the initial point.

7. The hinge assembly of claim 6, wherein angular displacement of the proximal member relative to the distal member from the initial point in the second direction compresses the second elastomeric spring to dampen the angular displacement in the second direction, and decompression of the second elastomeric spring urges angular displacement of the proximal member relative to the distal member in the first direction back to the initial point.

8. The hinge assembly of claim 6, wherein the second elastomeric spring decompresses when the first elastomeric spring compresses.

9. The hinge assembly of claim 6, wherein the first elastomeric spring decompresses when the second elastomeric spring compresses.

10. The hinge assembly of claim 6, wherein the first and the second elastomeric springs compress against inner walls of the spring channel to dampen angular displacement.

11. A hinge assembly comprising:
   a first member movably connected to a second member to allow angular displacement of the first member relative to the second member in each of extension and flexion directions;
   at least one elastomeric spring communicating with the first and the second members, wherein the at least one elastomeric spring is configured to restrain angular displacement from an extension to a flexion position, and from a flexion to an extension position, through compression of the at least one elastomeric spring, and to assist angular displacement from a flexion to an extension position, and from an extension to a flexion position, through decompression of the at least one elastomeric spring.

12. The hinge assembly of claim 11, wherein the at least one elastomeric spring is adapted to provide a pre-determined force deflection curve in compression and an independent rate of return hysteresis in decompression.

13. The hinge assembly of claim 11, wherein a time rate of compression of the at least one elastomeric spring in response to a certain force is faster than a subsequent time rate of decompression of the at least one elastomeric spring resulting from the certain force.

14. The hinge assembly of claim 11, wherein angular displacement is restrained over a predetermined angular range in each of the flexion and extension positions from a user selected initial point.

15. The hinge assembly of claim 14, wherein returning angular displacement is assisted back to the user selected initial point.

16. A hinge assembly comprising:
a proximal member movably connected to a distal member to allow angular displacement of the proximal member relative to the distal member;
a first and a second spring housing communicating with the proximal and the distal members, wherein movement of the first and the second spring housings track movement of one or both of the proximal and the distal members; and
a first elastomeric spring in bearing engagement with the first spring housing, and a second elastomeric spring in bearing engagement with the second spring housing, wherein angular displacement of the proximal member relative to the distal member from an initial point in a first direction compresses the first elastomeric spring to dampen the angular displacement in the first direction, and decompression of the first elastomeric spring urges angular displacement of the proximal member relative to the distal member in a second direction back to the initial point.

17. The hinge assembly of claim 16, wherein angular displacement of the proximal member relative to the distal member from the initial point in the first direction compresses both the first and the second elastomeric springs to dampen the angular displacement in the first direction, and decompression of the first and the second elastomeric springs urge angular displacement of the proximal member relative to the distal member in the second direction back to the initial point.

18. The hinge assembly of claim 16, wherein angular displacement of the proximal member relative to the distal member from the initial point in the second direction compresses the second elastomeric spring to dampen the angular displacement in the second direction, and decompression of the second elastomeric spring urges angular displacement of the proximal member relative to the distal member in the first direction back to the initial point.

19. The hinge assembly of claim 16, wherein angular displacement of the proximal member relative to the distal member from the initial point in the second direction compresses both the first and the second elastomeric springs to dampen the angular displacement in the second direction, and decompression of the first and the second elastomeric springs urge angular displacement of the proximal member relative to the distal member in the first direction back to the initial point.

20. The hinge assembly of claim 16, wherein the elastomeric springs are made of urethane.

21. The hinge assembly of claim 11, further comprising:
a spring housing communicating with the first and the second members, where the at least one elastomeric spring resides within the spring housing;
pins residing within the spring housing that communicate with the at least one elastomeric spring, the pins extending from the spring housing and into guide slots associated with, and fixed in relation to, either one of the first or the second member; wherein:
angular displacement of the first member relative to the second member, in either an extension or flexion direction, causes each elastomeric spring to compress within a respective channel of the spring housing, due to bearing engagement of the spring with a respective pin moving within the channel of the spring housing due to bearing engagement of the respective pin within a respective guide slot.

22. The hinge assembly of claim 21, wherein the other one of the first or the second member is movably connected to the spring housing, allowing user selection of an initial radial point, between the first and the second members, to begin dampening of angular displacement of the first member relative to the second member in each of extension and flexion directions.

23. A hinge assembly, comprising:
a proximal member movably connected to a distal member to allow angular displacement of the proximal member relative to the distal member in each of extension and flexion directions;
a spring housing communicating with the proximal and the distal members, having at least one internal spring channel defined by walls, and having a toothed exterior;
a lock plate linearly translatable relative to one of the proximal or the distal members, the lock plate having one or more slide teeth, the one or more slide teeth configured to engage the toothed exterior of the spring housing;
at least one elastomeric spring, each spring housed in a respective internal channel of the spring housing; and
at least two pusher pins, where two pusher pins are in bearing engagement with each spring within the respective internal channel, the at least two pusher pins further extending from the internal channel into guide slots associated with, and fixed in relation to, the other one of the proximal or the distal members, wherein:
angular displacement of the proximal member relative to the distal member, with the lock plate engaged to the spring housing, in either an extension or a flexion direction, causes one pusher pin to compress the at least one spring against the walls of the respective internal channel, due to bearing engagement of the one pusher pin within a respective guide slot, to dampen the angular displacement, wherein decompression of the at least one spring against the respective pusher pin urges return angular displacement.

* * * * *